(12) United States Patent
Gao et al.

(10) Patent No.: US 8,470,771 B2
(45) Date of Patent: Jun. 25, 2013

(54) METHOD AND MEDICAMENT FOR INHIBITING THE INFECTION OF INFLUENZA VIRUS

(75) Inventors: George Fu Gao, Beijing (CN); June Liu, Beijing (CN); Po Tien, Beijing (CN)

(73) Assignee: Institute of Microbiology, Chinese Academy of Sciences, Beijing (CN)

( * ) Notice: Subject to any disclaimer, the term of this patent is extended or adjusted under 35 U.S.C. 154(b) by 377 days.

(21) Appl. No.: 12/743,028

(22) PCT Filed: Dec. 18, 2007

(86) PCT No.: PCT/CN2007/003651
§ 371 (c)(1),
(2), (4) Date: May 14, 2010

(87) PCT Pub. No.: WO2009/062348
PCT Pub. Date: May 22, 2009

(65) Prior Publication Data
US 2010/0249021 A1   Sep. 30, 2010

(30) Foreign Application Priority Data

Nov. 14, 2007 (CN) .......................... 2007 1 0177317

(51) Int. Cl.
*A61K 38/00* (2006.01)
*A01N 37/18* (2006.01)
(52) U.S. Cl.
USPC ........................................................ 514/3.7

(58) Field of Classification Search
None
See application file for complete search history.

(56) References Cited

U.S. PATENT DOCUMENTS

| 4,625,015 | A | * | 11/1986 | Green et al. .................. 530/324 |
| 7,504,109 | B2 | * | 3/2009 | Yang et al. .................. 424/206.1 |
| 2007/0042002 | A1 | | 2/2007 | Weeks-Levy et al. |

FOREIGN PATENT DOCUMENTS

| CN | 1488641 A | 4/2004 |
| CN | 1709912 A | 12/2005 |
| WO | WO 2006/069262 A2 | 6/2006 |
| WO | WO 2007/011904 A2 | 1/2007 |
| WO | WO 2007/095318 A2 | 8/2007 |

OTHER PUBLICATIONS

Thomas A., et al Prediction of peptide structure: how far are we? Proteins. Dec. 1, 2006;65(4):889-97.*

* cited by examiner

*Primary Examiner* — Thomas Heard
(74) *Attorney, Agent, or Firm* — Knobbe, Martens, Olson & Bear, LLP

(57) ABSTRACT

The invention relates to a process for inhibiting the infection of influenza viruses and a polypeptide or protein medicine used therein. More particularly, the invention involves a process for inhibiting the highly pathogenic avian influenza virus (such as H5N1 subtype) infection and human influenza virus (such as H1N1 subtype and H3N2 subtype) infection, as well as the polypeptide or protein involved therein, and a polynucleotide encoding the polypeptide or protein and a vector or host cell expressing said polypeptide or protein.

12 Claims, 6 Drawing Sheets

1, MDCK
2, MDCK/EGFP (27 kDa)
3, MDR1 (36 kDa)
4, MDR2 (40 kDa)
M, protein molecular weight marker

SEQUENCE LISTING

```
<160> NUMBER OF SEQ ID NOS: 48

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide

<400> SEQUENCE: 1

Lys Glu Ser Thr Gln Lys Ala Ile Asp Gly Val Thr Asn Lys Val Asn
1               5                   10                  15

Ser Ile Ile Asp Lys
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide

<400> SEQUENCE: 2

Lys Glu Ser Thr Gln Lys Ile Ile Asp Gly Val Thr Asn Lys Val Asn
1               5                   10                  15

Ser Ile Ile Asp Lys
            20

<210> SEQ ID NO 3
<211> LENGTH: 25
<212> TYPE: PRT
<213> ORGANISM: Artificial Sequence
<220> FEATURE:
<223> OTHER INFORMATION: Synthetic peptide

<400> SEQUENCE: 3

Lys Glu Ser Thr Gln Lys Ala Ile Asp Gly Val Thr Ala Ala Ala Ala
1               5                   10                  15

Asn Lys Val Asn Ser Ile Ile Asp Lys
            20                  25

<210> SEQ ID NO 4
<211> LENGTH: 51
<212> TYPE: PRT
<213> ORGANISM: Artificial Sequence
<220> FEATURE:
<223> OTHER INFORMATION: Synthetic peptide

<400> SEQUENCE: 4

Arg Arg Ile Glu Asn Leu Asn Lys Lys Met Glu Asp Gly Phe Leu Asp
```

```
                1               5                   10                  15
Val Trp Thr Tyr Asn Ala Glu Leu Leu Val Leu Met Glu Asn Glu Arg
                                20                  25                  30

Thr Leu Asp Phe His Asp Ser Asn Val Lys Asn Leu Tyr Asp Lys Val
            35                  40                  45

Arg Leu Gln
    50

<210> SEQ ID NO 5
<211> LENGTH: 51
<212> TYPE: PRT
<213> ORGANISM: Artificial Sequence
<220> FEATURE:
<223> OTHER INFORMATION: Synthetic peptide

<400> SEQUENCE: 5

Arg Arg Ile Glu Asn Leu Asn Lys Lys Met Glu Asp Gly Ala Leu Asp
1               5                   10                  15

Val Trp Thr Tyr Asn Ala Glu Ala Leu Val Leu Met Glu Asn Glu Arg
                                20                  25                  30

Thr Leu Asp Phe His Asp Ser Asn Val Lys Asn Leu Tyr Asp Lys Val
            35                  40                  45

Arg Leu Gln
    50

<210> SEQ ID NO 6
<211> LENGTH: 18
<212> TYPE: PRT
<213> ORGANISM: Artificial Sequence
<220> FEATURE:
<223> OTHER INFORMATION: Synthetic peptide

<400> SEQUENCE: 6

Ser Ser Ser Ser Gly Gly Ser Ser Gly Gly Ser Ser Gly Gly Ser Ser
1               5                   10                  15

Gly Ser

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide

<400> SEQUENCE: 7

Ala Ala Ala Ala Ala Gly Gly Gly Gly Ala Ala Ala Ala Ala
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic peptide

<400> SEQUENCE: 8

Gly Gly Gly Gly Gly Ala Ala Ala Ala Gly Gly Gly Gly Gly
1               5                   10

<210> SEQ ID NO 9
<211> LENGTH: 15
<212> TYPE: PRT
<213> ORGANISM: Artificial Sequence
<220> FEATURE:
```

<223> OTHER INFORMATION: Synthetic peptide

<400> SEQUENCE: 9

Gly Gly Gly Gly Gly Ser Ser Ser Ser Gly Gly Gly Gly Gly
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Gly Ser Gly Ser Gly Ser Gly Ser Gly Ser Gly Ser Gly Ser Gly
1               5                   10                  15

<210> SEQ ID NO 11
<211> LENGTH: 225
<212> TYPE: PRT
<213> ORGANISM: Artificial Sequence
<220> FEATURE:
<223> OTHER INFORMATION: Synthetic peptide

<400> SEQUENCE: 11

Lys Glu Ser Thr Gln Lys Ala Ile Asp Gly Val Thr Asn Lys Val Asn
1               5                   10                  15

Ser Ile Ile Asp Lys Gly Ser Gly Ser Gly Ser Gly Ser Gly
                20                  25                  30

Ser Gly Ser Gly Arg Arg Ile Glu Asn Leu Asn Lys Lys Met Glu Asp
            35                  40                  45

Gly Phe Leu Asp Val Trp Thr Tyr Asn Ala Glu Leu Leu Val Leu Met
    50                  55                  60

Glu Asn Glu Arg Thr Leu Asp Phe His Asp Ser Asn Val Lys Asn Leu
65              70                  75                  80

Tyr Asp Lys Val Arg Leu Gln Gly Ser Gly Ser Gly Ser Gly Ser Gly
                85                  90                  95

Ser Gly Ser Gly Ser Gly Lys Glu Ser Thr Gln Lys Ala Ile Asp Gly
            100                 105                 110

Val Thr Asn Lys Val Asn Ser Ile Ile Asp Lys Gly Ser Gly Ser Gly
            115                 120                 125

Ser Gly Ser Gly Ser Gly Ser Gly Arg Arg Ile Glu Asn Leu
            130                 135                 140

Asn Lys Lys Met Glu Asp Gly Phe Leu Asp Val Trp Thr Tyr Asn Ala
145                 150                 155                 160

Glu Leu Leu Val Leu Met Glu Asn Glu Arg Thr Leu Asp Phe His Asp
                165                 170                 175

Ser Asn Val Lys Asn Leu Tyr Asp Lys Val Arg Leu Gln Gly Ser Gly
                180                 185                 190

Ser Gly Ser Gly Ser Gly Ser Gly Ser Gly Lys Glu Ser Thr
            195                 200                 205

Gln Lys Ala Ile Asp Gly Val Thr Asn Lys Val Asn Ser Ile Ile Asp
    210                 215                 220

Lys
225

<210> SEQ ID NO 12
<211> LENGTH: 63
<212> TYPE: DNA
<213> ORGANISM: Artificial Sequence

```
<220> FEATURE:
<223> OTHER INFORMATION: Synthetic oligonucleotide

<400> SEQUENCE: 12
aaagaatcca ctcaaaaggc aatagatgga gtcaccaata aggtcaactc gatcattgac    60
aaa                                                                  63

<210> SEQ ID NO 13
<211> LENGTH: 153
<212> TYPE: DNA
<213> ORGANISM: Artificial Sequence
<220> FEATURE:
<223> OTHER INFORMATION: Synthetic oligonucleotide

<400> SEQUENCE: 13
aggagaatag aaaatttaaa caagaagatg gaagacggat tcctagatgt ctggacttat    60
aatgctgaac ttctggttct catggaaaat gagagaactc tagactttca tgactcaaat   120
gtcaagaacc tttacgacaa ggtccgacta cag                                153

<210> SEQ ID NO 14
<211> LENGTH: 675
<212> TYPE: DNA
<213> ORGANISM: Artificial Sequence
<220> FEATURE:
<223> OTHER INFORMATION: Synthetic oligonucleotide

<400> SEQUENCE: 14
aaagaatcca ctcaaaaggc aatagatgga gtcaccaata aggtcaactc gatcattgac    60
aaaggcagtg gaagcggtag cggtagtgga agcggtagcg gtagcggtag gagaatagaa   120
aatttaaaca agaagatgga agacggattc tagatgtct ggacttataa tgctgaactt   180
ctggttctca tggaaaatga gagaactcta gactttcatg actcaaatgt caagaacctt   240
tacgacaagg tccgactaca gggcagtgga agcggtagcg gtagtggaag cggtagcggt   300
agcggtaaag aatccactca aaaggcaata gatggagtca ccaataaggt caactcgatc   360
attgacaaag gcagtggaag cggtagcggt agtggaagcg gtagcggtag cggtaggaga   420
atagaaaatt taaacaagaa gatggaagac ggattcctag atgtctggac ttataatgct   480
gaacttctgg ttctcatgga aaatgagaga actctagact ttcatgactc aaatgtcaag   540
aacctttacg acaaggtccg actacagggc agtggaagcg gtagcggtag tggaagcggt   600
agcggtagcg gtaaagaatc cactcaaaag gcaatagatg gagtcaccaa taaggtcaac   660
tcgatcattg acaaa                                                    675

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
gcaaaagcag gggtctgatc tgtc                                           24

<210> SEQ ID NO 16
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 16
```
agtagaaaca agggtgtttt taactac                                              27

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
gcaaaagcag gagttcaaaa tg                                                   22

<210> SEQ ID NO 18
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 18
agtagaaaca aggagttttt tgaacagact acttg                                     35

<210> SEQ ID NO 19
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 19
atatcgtctc gtattagtag aaacaagg                                             28

<210> SEQ ID NO 20
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 20
tattcgtctc ggggagcaaa agcagggg                                             28

<210> SEQ ID NO 21
<211> LENGTH: 20
<212> TYPE: PRT
<213> ORGANISM: Artificial Sequence
<220> FEATURE:
<223> OTHER INFORMATION: Synthetic peptide

<400> SEQUENCE: 21

Arg Arg Ile Glu Asn Leu Asn Lys Lys Met Glu Asp Gly Phe Leu Asp
1               5                   10                  15

Val Trp Thr Tyr
            20

<210> SEQ ID NO 22
<211> LENGTH: 23
<212> TYPE: PRT
<213> ORGANISM: Artificial Sequence
<220> FEATURE:
<223> OTHER INFORMATION: Synthetic peptide

<400> SEQUENCE: 22

Asn Ala Glu Leu Leu Val Leu Met Glu Asn Glu Arg Thr Leu Asp Phe
1               5                   10                  15

His Asp Ser Asn Val Lys Asn
            20

<210> SEQ ID NO 23
<211> LENGTH: 16
<212> TYPE: PRT
<213> ORGANISM: Artificial Sequence
<220> FEATURE:
<223> OTHER INFORMATION: Synthetic peptide

<400> SEQUENCE: 23

Phe His Asp Ser Asn Val Lys Asn Leu Tyr Asp Lys Val Arg Leu Gln
1               5                   10                  15

<210> SEQ ID NO 24
<211> LENGTH: 308
<212> TYPE: DNA
<213> ORGANISM: Artificial Sequence
<220> FEATURE:
<223> OTHER INFORMATION: Synthetic oligonucleotide

<400> SEQUENCE: 24
ggggtaccac catgggggca ggtgccaccg gccgcgccat ggacgggccg cgcctgctgc      60
tgttgctgct tctgggggtg tcccttggag gtgccggatc caaagaatcc actcaaaagg    120
caatagatgg agtcaccaat aaggtcaact cgatcattga caagaattc gtgcccaggg     180 attgtggttg taagccttgc atatgtacac tcatccccgt ctattgctcc atcctggctg    240
ctgtggtggt gggccttgtg cctacatag ccttcaagag gtggaacagg ggcatcctgc     300
tcgagcgg                                                              308

<210> SEQ ID NO 25
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 25
ggggtaccac catgggggca ggtgccaccg gccgcgccat ggacgggccg cg             52

<210> SEQ ID NO 26
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 26
caagggacac ccccagaagc agcaacagca gcaggcgcgg cccgtccatg g              51

<210> SEQ ID NO 27
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 27 ctggggtgt cccttggagg tgccggatcc aaagaatcca ctcaaaaggc                 50

<210> SEQ ID NO 28
<211> LENGTH: 53
<212> TYPE: DNA
<213> ORGANISM: Artificial Sequence
<220> FEATURE:

<223> OTHER INFORMATION: Synthetic oligonucleotide

<400> SEQUENCE: 28
caatgatcga gttgacctta ttggtgactc catctattgc cttttgagtg gat    53

<210> SEQ ID NO 29
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 29
gtcaactcga tcattgacaa agaattcgtg cccagggatt gtggttgtaa gcc    53

<210> SEQ ID NO 30
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 30
ggatggagca atagacgggg atgagtgtac atatgcaagg cttacaacca caat    54

<210> SEQ ID NO 31
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 31
gtctattgct ccatcctggc tgctgtggtg gtgggccttg tggcctacat agcc    54

<210> SEQ ID NO 32
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 32
ccgctcgagc aggatgcccc tgttccacct cttgaaggct atgtaggcca ca    52

<210> SEQ ID NO 33
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 33
cgagatctac caccatgggg gcaggtg    27

<210> SEQ ID NO 34
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 34
tgcactgcag caggatgccc ctgttccac    29

<210> SEQ ID NO 35

```
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 35
cgggatccag gagaatagaa aatttaaac                                          29

<210> SEQ ID NO 36
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 36
cggaattcct gtagtcggac cttgtcg                                            27

<210> SEQ ID NO 37
<211> LENGTH: 1707
<212> TYPE: DNA
<213> ORGANISM: Artificial Sequence
<220> FEATURE:
<223> OTHER INFORMATION: Synthetic oligonucleotide

<400> SEQUENCE: 37
atggagaaaa tagtgcttct tcttgcaata gtcagtcttg ttaaaagtga tcagatttgc          60
attggttacc atgcaaacaa ctcgacagag caggttgaca caataatgga aaagaacgtc         120
actgttacac acgcccaaga catactggaa agacacacac acgggaagct ctgcgatcta         180
gatggagtga agcctctaat tttaagagat tgtagtgtag ctggatggct cctcgggaac         240
ccaatgtgtg acgaattcct caatgtgccg gaatggtctt acatagtgga agagatcaat         300
ccagccaatg acctctgtta cccagggaat tcaacgact atgaagaact gaaacaccta         360
ttgagcagaa taaccatttt tgagaaaatt cagatcatcc ccaaaagttc ttggtcagat         420
catgaagcct catcagggt gagctcagca tgtccatacc agggaaggtc ctcctttttt         480
agaaatgtgg tatggcttat caaaaagaac aatgcatacc caacaataaa gagaagttac         540 ataatacca accaagaaga tcttttggta ctgtggggga ttcaccatcc aaatgatgcg         600
gcagagcaga caaggctcta tcaaaaccca accacctata tttccgttgg gacatcaaca         660
ctaaaccaga gattggtacc aaaaatagct actagatcca aggtaaacgg caaagtggaa         720
aggatggagt tcttttggac aattttaaaa ccgaatgatg caataaactt tgagagtaat         780
ggaaatttca ttgctccaga aaatgcatac aaaattgtca gaaaggggga ctcaacaatt         840
atgaaaagtg aattggaata tggtaactgc aacaccaagt gtcaaactcc aatagggggcg         900 ataaactcta gtatgccatt ccacaacatc caccctctca ccatcgggga atgccccaaa         960
tatgtgaaat caaacagatt aatcctcgcg actgggctca gaaatagccc tcaaggagag        1020
agaagaagaa aaagagaggg actatttgga gctatagcag gttttataga gggaggatgg        1080
cagggaatgg tagatggttg gtatgggtac caccatagca acgagcaggg gagtgggtac        1140
gctgcagaca agaatccac tcaaaaggca atagatggag tcaccaataa ggtcaactcg        1200
atcattgaca aaatgaacac tcagtttgag gccgttggaa gggaatttaa taacttagaa        1260
aggagaatag aaaatttaa caagaagatg gaagacggat tcctagatgt ctggacttat        1320
aatgctgaac ttctggttct catggaaaat gagagaactc tagactttca tgactcaaat        1380
gtcaagaacc tttacgacaa ggtccgacta cagcttaggg ataatgcaaa ggagcttggt        1440
```

```
aacggttgtt tcgagttcta tcacagatgt gataatgaat gtatggaaag tgtaagaaac    1500
ggaacgtatg actacccgca gtattcagaa gaagcaagat taaaaagaga ggaaataagt    1560
ggagtaaaat tggaatcaat aggaacttac caaatactgt caatttattc aacagtggcg    1620
agctccctag cactggcaat catggtggct ggtctatctt tatggatgtg ctccaatgga    1680
tcgttacaat gcagaatttg catttaa                                       1707
```

```
<210> SEQ ID NO 38
<211> LENGTH: 398
<212> TYPE: DNA
<213> ORGANISM: Artificial Sequence
<220> FEATURE:
<223> OTHER INFORMATION: Synthetic oligonucleotide

<400> SEQUENCE: 38
ggggtaccac catgggggca ggtgccaccg gccgcgccat ggacgggccg cgcctgctgc     60
tgttgctgct tctggggtg tcccttggag gtgccggatc caggagaata gaaaatttaa    120
acaagaagat ggaagacgga ttcctagatg tctggactta taatgctgaa cttctggttc    180
tcatggaaaa tgagagaact ctagactttc atgactcaaa tgtcaagaac ctttacgaca    240
aggtccgact acaggaattc gtgcccaggg attgtggttg taagccttgc atatgtacac    300
tcatccccgt ctattgctcc atcctggctg ctgtggtggt gggccttgtg gcctacatag    360
ccttcaagag gtggaacagg ggcatcctgc tcgagcgg                            398
```

```
<210> SEQ ID NO 39
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 39
ggaattccat atgtcaggtg gaggtaccag gagaatagaa aat                       43
```

```
<210> SEQ ID NO 40
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 40
cgggatcccg aactaccgcc cgagcttcca cctgaactgc caccctgtag tcggacctt      59
```

```
<210> SEQ ID NO 41
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 41
cggaattcgg tggcagttca ggtggaagct cgggcggtag ttcgaggaga atagaaaat      59
```

```
<210> SEQ ID NO 42
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 42
```

```
ccgctcgaga cctccgctag atctctgtag tcggaccttg tc                42
```

<210> SEQ ID NO 43
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 43

```
ggaattccat atgaaagaat ccactc                                  26
```

<210> SEQ ID NO 44
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 44

```
ggggtacctg agctggacga actaccgccc                              30
```

<210> SEQ ID NO 45
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 45

```
gaagatcttc aagctccggt ggcagttcag                              30
```

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 46

```
ccgctcgagt ttgtcaatga tcgag                                   25
```

<210> SEQ ID NO 47
<211> LENGTH: 702
<212> TYPE: DNA
<213> ORGANISM: Artificial Sequence
<220> FEATURE:
<223> OTHER INFORMATION: Synthetic oligonucleotide

<400> SEQUENCE: 47

```
atgaaagaat ccactcaaaa ggcaatagat ggagtcacca ataaggtcaa ctcgatcatt    60
gacaaagaat tcggtggcag ttcaggtgga agctcgggcg gtagttcgtc cagctcaggt   120
accaggagaa tagaaaattt aaacaagaag atggaagacg gattcctaga tgtctggact   180
tataatgctg aacttctggt tctcatggaa aatgagagaa ctctagactt tcatgactca   240
aatgtcaaga acctttacga caaggtccga ctacagggtg gcagttcagg tggaagctcg   300
ggcggtagtt cgggatccaa agaatccact caaaaggcaa tagatggagt caccaataag   360
gtcaactcga tcattgacaa agaattcggt ggcagttcag gtggaagctc gggcggtagt   420
tcgaggagaa tagaaaattt aaacaagaag atggaagacg gattcctaga tgtctggact   480
tataatgctg aacttctggt tctcatggaa aatgagagaa ctctagactt tcatgactca   540
aatgtcaaga acctttacga caaggtccga ctacagagat cttcaagctc cggtggcagt   600
```

-continued

```
tcaggtggaa gctcgggcgg tagttcggga tccaaagaat ccactcaaaa ggcaatagat      660
ggagtcacca ataaggtcaa ctcgatcatt gacaaactcg ag                        702

<210> SEQ ID NO 48
<211> LENGTH: 1350
<212> TYPE: DNA
<213> ORGANISM: Artificial Sequence
<220> FEATURE:
<223> OTHER INFORMATION: Synthetic oligonucleotide

<400> SEQUENCE: 48
atgaatccaa atcagaagat aataaccatc ggatcaatct gtatggtaat tggaatagtt      60
agcttaatgt tacaaattgg aacatgatc tcaatatggg tcagtcattc aattcagaca     120
gggaatcaac gccaagctga accaatcagc aatactaaat ttcttactga gaaagctgtg    180
gcttcagtaa cattagcggg caattcatct ctttgcccca ttagcggatg ggctgtatac    240
agtaaggaca cagtataag gatcggttcc aggggggatg tgtttgttat aagagagccg     300
ttcatctcat gctcccactt ggaatgcaga actttctttt tgactcaggg agccttgctg    360
aatgacaagc actccaatgg gactgtcaaa gacagaagcc ctcacagaac attaatgagt    420
tgtcctgtgg gtgaggctcc ctccccatat aactcaaggt ttgagtctgt tgcttggtca    480
gcaagtgctt gccatgatgg caccagttgg ttgacaattg gaatttctgg tccagacaat    540
ggggctgtgg ctgtattgaa atacaatggc ataataacag acaccatcaa gagttggagg    600
aacaacatac tgagaactca agagtctgaa tgtgcatgtg taaatggctc ttgctttact    660
gtaatgactg atggaccaag taatgggcag gcatcatata agatcttcaa aatggaaaaa    720
gggaaagtgg ttaaatcagt cgaattggat gctcctaatt atcactatga ggagtgctcc    780
tgttatcctg atgccggcga aatcacatgt gtgtgcaggg ataattggca tggcttaaat    840
aggccatggg tatctttcaa tcaaaatttg gagtatcaaa taggatatat atgcagtgga    900
gttttcggag acaatccacg ccccaatgat ggaacaggta gttgtggtcc ggtgtcccct    960
aacggggcat atggggtaaa agggttttca tttaaatacg gcaatggtgt ctggatcggg   1020
agaaccaaaa gcactaattc caggagcggc tttgaaatga tttgggatcc aaatgggtgg   1080
actggaacgg acagtagctt ttcggtgaag caagatatcg tagcaataac tgattggtca   1140
ggatatagcg ggagttttgt ccagcatcca gaactgacag gattagattg cataagacct   1200
tgtttctggg ttgagttaat cagagggcgg cctaaagaga gcacaatttg gaccagtggg   1260
agcagcatat ctttttgtgg tgtaaatagt gacactgtta gttggtcttg gccagacggt   1320
gctgagttgc cattcaccat tgacaagtag                                    1350
```

METHOD AND MEDICAMENT FOR INHIBITING THE INFECTION OF INFLUENZA VIRUS

RELATED APPLICATIONS

This application is a U.S. National Phase of International Application No.: PCT/CN2007/003651, filed Dec. 18, 2007, designating the U.S. and published in Chinese on May 22, 2009 as WO 2009/062348 A1, which claims the benefit of Chinese Application No. 200710177317.2, filed Nov. 14, 2007.

FIELD OF THE INVENTION

The invention relates to a method for treating the infection of enveloped viruses and a polypeptide or protein medicine used in the field of biomedical techniques. More particularly, the invention involves a method for treating the infection of influenza viruses, especially the highly pathogenic avian influenza virus (such as H5N1 subtype) and human influenza virus (such as H1N1 subtype and H3N2 subtype), as well as the polypeptide or protein involved therein, and a nucleic acid encoding said polypeptide or protein and a vector or cell expressing said polypeptide or protein.

BACKGROUND OF THE INVENTION

Viral infection is not only extremely harmful to human health, but also severely endangers the survival and breeding of various animals, and thus becoming an important research task in medical and relevant fields currently. Investigation and invention of a medicine for treating viral infection has a significant application potential. Therefore, once succeeds, it will generate a huge social and economic benefit.

Influenza (shortened as "flu") is the most rampant infectious disease in the world. This acute infectious disease of upper respiratory tract has some features, such as a strong infectivity, a rapid spreading ability, a short latent period, and a high morbidity. And influenza is a viral infectious disease commonly suffered in human, avian and livestock. Pandemic influenza occurred several times in the past: the pandemic influenza of 1918 in Spain, which claimed 50 million lives; the pandemic influenza of 1957, which led to 15 hundred millions infected globally. The morbidity, mortality as well as social and personal economic damage caused by influenza are still ranked as No. 1 in all infectious diseases, which brings a huge calamity to human. Influenza is a frequently occurred disease in China. In fact, several pandemics of influenza since 1957 originated from China (Yuanji Guo, Xiaowen Cheng, 1997). Therefore, prophylaxis and treatment of influenza is well appreciated in China.

Influenza virus is the pathogen causing influenza, which belongs to Orthomyxoviridae family, and is a negative-strand RNA virus varying frequently. Highly Pathogenic Avian Influenza Virus (HPAIV), which has drawn a lot of attention for these years, is a highly contact acute infectious disease caused by influenza A virus. It causes many lethal pathologic changes to both domestic fowls and wild birds, including the pathologic change of respiratory systems to systematic septemia. Worldwide scale pandemics of HPAIV have occurred many times. Even worse, the unprecedented infection of avian influenza virus subtype H5N1 in human has occurred several times for the past a few years, and resulted in death of patients (Kamps et al, 2006). The possibility of highly pathogenic avian influenza virus to spread among human by crossing the barrier between species and to cause a new round worldwide pandemic makes all countries attach importance to the prophylaxis and treatment of the highly pathogenic avian influenza. HPAIV has been ranked as a category A infectious disease by Office International Des Epizooties (OIE), and listed as one of the animal infectious diseases in International Biological Weapon Treaty. HPAIV was also ranked as a category A monitored infectious disease by Department of Agriculture in China.

Influenza virus is essentially consisted of envelope and nucleocapsid, wherein the envelope is composed of spike, bilayer lipid membrane and matrix protein (M). The spike is divided into two categories: one is rod-shaped and consisted of trimers of hemagglutinin (HA) protein; the other is mushroom-shaped and consisted of tetramers of neuraminidase (NA). The bilayer lipid membrane is obtained from host cells membrane while the virion is budding. The matrix protein is closely lined up at the inner side of the envelope, and is a structural protein maintaining the viral shape. The nucleocapsid, coated by the matrix protein, is consisted of 8 RNA-nucleoprotein complexes (RNP) arranged in a helix shape. Each RNP is consisted of monomer negative-strand RNA coated with nucleoprotein (NP). The 8 negative-strand RNAs in influenza virus genome thus constitute 8 RNPs. According to the different antigenicity between nucleoprotein NP and matrix protein M, influenza virus is divided into 3 types, i.e. A, B and C. The 3 types of influenza virus do not share any common antigen, but all infect human. Among them, influenza A virus has the biggest pandemic scale. Each type of influenza virus is further divided into many subtypes according to the different antigenicity of hemagglutinin (HA; shortly as "H") and neuraminidase (NA; shortly as "N") at the viral surface. There has been found 16 subtypes of H, 9 subtypes of N in influenza A virus. Subtype H and N may constitute various combinations, such as H1N1, H5N1, H3N2, and H9N2, etc.

Since 1918, it has been witnessed several worldwide pandemic and some epidemic of influenza caused by influenza virus. Influenza virus is very rampant, since it constantly varies. The reasons causing the variation mainly include: 1) influenza virus genome is consisted of negative-strand RNA and RNA replicase lacks of a correction function during the genomic replication, therefore it is very easy for the viral genome to be varied during the replication in host cells, which leads to the variation of the amino acids encoded by it and thereby leads to an antigen shift; 2) influenza virus genome is consisted of 8 of segmented RNAs, and the 8 segments can be randomly reassorted while one cell is infected with various influenza virion. Theoretically, $2^8$ (256) of new viral strains with completely different antigenicity and pathogenicity may be formed through the gene reassortment, therefore an antigen shift will occur, which enables influenza virus to escape the monitor of the immune system, to replicate in a large scale in host cells, and to cause new pandemic of influenza. As a result, the antigen of influenza virus varies rapidly and the reassortment rate among different influenza viral strains is very high, which leads to a huge challenge to the prophylaxis and treatment of influenza virus.

Vaccination of influenza virus is the first strategy for preventing human influenza currently. However, influenza virus has many serotypes, so if the antigenicity between the vaccine strain and epidemic strain does not match each other, the vaccine will lose its function, and may not provide corresponding protection. On the other hand, since influenza virus varies frequently, the speed of vaccine development is far behind that of influenza virus variation. In fact, when a new epidemic strain appears, at least 6 months are required for producing its corresponding vaccine (Kamps et al, 2006), which makes the preparation of vaccines always in a passive position. In this case, neither a traditional inactivated vaccine nor a novel vaccine such as genetic engineering vaccine, a nucleic acid vaccine and the like can provide crossing protection for all types of influenza virus. Moreover, the protection period for influenza vaccines is very short, i.e. only half a year to a year, so these vaccines need to be injected every year, which is hard to be accepted by the patients. However, regarding vaccines for the highly pathogenic avian influenza virus, a policy for forbidding or not advocating the utilization of such vaccines is taken in many countries, so as to avoid frequently occurred variation of the viral antigens caused under a selective pressure of hosts. The use of such vaccines is also under disputation in academia (Kamps et al, 2006).

Due to the relatively poor effect of vaccines on prophylaxis of influenza, the investigation of pharmaceuticals for preventing and treating influenza virus has drawn a lot of attention. Till now, it has already gained some advances in development and research of the pharmaceuticals designed upon the molecular mechanism regarding viral infection and replication.

There are two classes of chemotherapeutic agents for influenza: (1) ion channel inhibitor, i.e. Amantadine and Rimantadine targeting the ion channel protein M2 of influenza virus, which prevent the replication of influenza virus by interfering the ion channel activity of influenza virus M2 protein (Skehel, 1992). Although such a chemotherapeutic agent results in certain therapeutic effect, a large amount of drug-resistant influenza virus strains have appeared (Jefferson et al, 2006), and such agent causes more severe toxic side effect. As a result, the specialists in WHO have suggested to stop using M2 ion channel inhibitors as anti-influenza medicines (Kamps et al; 2006). (2) neuraminidase inhibitor, i.e. an inhibitor targeting NA of influenza virus, such as 4-guanidino-2,4-deoxy-2,3-dehydro-N-acetylneuraminicacid (4-guanidino-Neu5Acen) and an analog thereof, which may effectively inhibit the release of virion at the host cell surface by inhibiting the activity of NA, thereby preventing other host cells from being infected with influenza virus. Such chemotherapeutic agents, with the trade names of Zanamivir and Oseltamivir, are used to treat influenza virus in USA and Australia, etc. Leneva et al. (2001) carried out an in vitro experiment using an influenza virus-sensitive cell line, i.e. MDCK, which showed that the 50% effect concentration ($EC_{50}$) of Zanamivir is 8.5-14.0 µM for the 3 subtypes of virus i.e. H5N1, H6N1 and H9N2. Although such agent has less toxic side effect than ion channel inhibitor, the corresponding drug-resistant strains also appeared (Abed et al, 2006), especially in the patients infected with avian influenza virus H5N1 (de Jong, 2005). (3) artificially synthesized sialosyl oligosaccharide analog, such as analogs of sialosyl glucoside liposome, sialosyl glucoside multimer, and bi-valence sialosyl glucoside, etc, which competitively binds to HA, thereby prohibiting HA from binding to the surface receptors on the host cell membrane, interfering the viral adsorption, and thereby suppressing the viral function. Till now, such suppression has been confirmed in an in vitro experiment (Haolong Pang et al, 2004), but in vivo data has not been reported, and the corresponding commercial medicines are not available. (4) A variety of anti-influenza A virus single-component and compound preparations of Chinese medicines, mainly including exterior-releasing medicines and heat-clearing and detoxifying medicines, have been screened out (Weimin Zhang et al, 2001) as a supportive therapy and they are not the inhibitors specified for influenza virus. Additionally, administration of Chinese medicine is so inconvenient that it can be only accepted by a few people. Moreover, the effect of Chinese medicine is still disputable in the western world. As a result, the anti-influenza virus Chinese medicines are very difficult to be widely used in a global extent.

There has gained some advance in the development of anti-influenza medicines using biotechnology. For example, in laboratory research, an oligonucleotide sequence synthesized or an expression vector constructed using anti-sense DNA technique, anti-sense RNA technique or RNA interfering technique (siRNA) show different levels of anti-influenza virus activities (Gao et al, 2006). However their corresponding commercial medicines are still not available. Some inter-related research indicated that the variation of siRNA targeting sequences would also result in appearance of the virus-tolerant strains. For instance, currently, a mutated drug-resistant strain has been found in the studies of anti-poliomyelitis virus and human immunodeficiency virus I (HIV-1) (Das et al, 2004).

At present, it shows a good prospect in the development of the anti-virus medicine by which a 7-peptide repeat region (Heptad Repeat, HR), i.e. a conserved region on main membrane protein of enveloped virus, is used as a target, wherein its mechanism is shown as follows: the critical step of infecting host cells with enveloped virus is the step of fusion of the membranes between the virus and the host cell, wherein the membrane fusion process is mediated by the fusion protein on the virus envelope. The fusion proteins can be divided into 2 groups, i.e. type I and II, based on their structural features. The virus containing fusion protein I is very common, including orthomyxovirus, paramyxovirus, coronavirus, retrovirus and filovirus, etc. The structure of fusion protein I comprises two regions of so called "7-peptide repeat (HR) sequence", wherein the one at the N-terminal of the fusion protein is designated as HR1, and the one at the C-terminal of the fusion protein is designated as HR2. These two sequences play important roles when fusion protein I exerts a membrane fusion activity. The locations and lengths of sequences HR1 and HR2 vary in different viruses. During the process of fusion, 3 of HR2s attach into the groove of a central trimer constituted with 3 of HR1s in an antiparrallel manner, thereby forming a stable 6-helix bundle or a structure called as a hairpin trimer. During the formation of such structure, the viral envelope and cell membrane may be drawn closer and then contacted with each other, which induces fusion of the membranes. The studies regarding HIV-1, SARS coronavirus (SARS-CoV), human respiratory syncytial virus (HRSV), and newcastle disease virus (NDV) show that the exogenously incorporated HR1 or HR2 polypeptides may inhibit infection of host cells with virus, wherein the mechanism thereof was presumed as follows: during the conformational variation of membrane proteins and the induction of membrane fusion, the exogenous polypeptides may competitively bind to the HR1 or HR2 on the virus fusion protein, thus interdicting the interaction between HR1 and HR2 of the virus fusion protein itself. Therefore, the hairpin trimer structure of the virus fusion protein could not be formed, which inhibits the fusion between viral envelope and cell membrane, thus preventing virus from entering into cells (Young et al, 1999; Wang et al, 2003; Greenberg et al, 2004). At the present, the polypeptide T-20 derived from the HR2 region on HIV-1 fusion protein gp41 was approved by the "express way" of Food and Medicine Administration (FDA) of USA, becoming the first anti-AIDS polypeptide medicine with excellent therapeutical effect for preventing HIV-1 from entering into cells. However, the artificial synthesis of such a polypeptide medicine is very expensive, and the treatment of HIV-1, a chronic infectious virus, requires a long term injection, so the injection of T-20 costs USD 20,000/year in USA, and USD 25,000/year in Europe. As a result, the application of T-20 is restricted by high cost. On the contrary, influenza virus causes transient but not long term chronic infection. In this case, if the prophylaxis and treatment by administration is timely performed before and after infection, it is possible to effectively control the progression of the disease, reduce infectivity, and decrease mortality of the infected subjects.

In view of the above, it is indicated that although there has gained some advance in the development and research of anti-influenza virus medicines, the tolerant strains for all commercialized chemical compound medicines appeared. Among the current anti-influenza medicines protected by patents, none of them is commercially available and is developed on the basis of biotechnology.

SUMMARY OF THE INVENTION

Facing the possibility of the highly pathogenic avian influenza virus to cross the barrier and spread among species and cause a new round worldwide pandemic influenza recently as well as the frequently occurred human influenza virus prevalence at present, the present inventor proposes a novel strategy for developing medicines with an function mechanism which is completely different from those of the current anti-influenza virus medicines. Such novel strategy utilizes the critical step of infecting host cells with influenza virus as the target, is based on the conformational change feature of influenza virus membrane protein HA before and after membrane fusion, and designs and synthesizes specific inhibitors (including polypeptides and proteins), which constitutes one of the novelty and inventive step of the invention. Secondly, there exist 2 types of membrane fusion of enveloped virus I. In the first type of membrane fusion, viral envelope fuses with host cell membrane directly and then releases the virus genome into the cytoplasm under a neutral pH; whereas in the second type of membrane fusion, after the endocytosis of the viruses into cells, viral envelope is induced to be fused with the membrane of the endocytic vesicle under a low pH condition in the endocytic vesicle, and then the virus genome is released into cytoplasm. The membrane fusion of all virus inhibited by HR1 or HR2 peptide inhibitors derived from the membrane protein of enveloped virus belongs to the first type of membrane fusion; whereas the membrane fusion of influenza virus belongs to the second type. As a result, the novelty and inventive step of the invention is also shown as such a first-time discovery that the viral infection belonging to the second type of membrane fusion may also be inhibited by HR1 and HR2 polypeptide inhibitors. The invention provides a new thought on screening of the inhibitors for similar virus.

The molecular mechanism is shown as follows: influenza virus is an enveloped virus and the envelope surface of influenza virus mainly comprises two types of membrane proteins, i.e. HA and NA, wherein HA functions at the critical step of infecting host cells with virus. HA is digested into two subunits after synthesized i.e. HA1 and HA2, wherein HA1 subunit constructs the head of HA protein and plays a role in the recognition of the receptor molecules (sialic acid) on host cell membrane surface; HA2 is located underneath the head formed by HA1 and is mainly associated with the fusion between the envelope of influenza virus and the membrane of the endocytic vesicles of host cells. During the infection of cells with influenza virus, the head (HA1 subunit) of membrane protein HA first recognizes the sialic acid receptor molecules on the membrane surface of host cells. Then the host cell membrane invaginates to form endocytic vesicles containing influenza virion into the cells. After the pH is decreased below 5.5 in the endocytic vesicles, the conformation of HA protein changes dramatically, HA1 trimers disassociate, and the fusion peptide at the N-terminal of HA2 is exposed and inserted into the membrane of endocytic vesicle. Subsequently, 3 of HR2s on HA2 subunit attach into the groove of a central trimer constituted with 3 of HR1s in an antiparrallel manner, thereby forming a stable 6-helix bundle. Finally, the viral envelope is induced to be fused with the membrane of the endocytic vesicle, so as to release the viral nucleocapsid into the cytoplasm, and start a viral replication process. Because the two 7-peptide repeat regions, i.e. HR1 and HR2, play important roles in the conformational variation process of HA protein, the inventor proposes that polypeptides and proteins may be designed and synthesized (or expressed) based on the sequences of the 7-peptide conserved regions HR1 and HR2 on the enveloped protein HA2 of the highly pathogenic avian influenza virus H5N1. The administration of such polypeptides and proteins can effectively inhibit the highly pathogenic avian influenza virus H5N1 subtype and human influenza virus H1N1 subtype, H3N2 subtype from infecting their respective sensitive cells— MDCK cells, so as to provide a novel anti-influenza virus (including human influenza virus and avian influenza virus) medicine.

In the invention, the inventor proposes a new anti-influenza virus inhibitor, which is a polypeptide or protein comprising a specified sequence and a gene encoding thereof, and a medicament of any combination of 1, 2 or more above components. According to the critical step of infecting host cells with influenza virus—a process of membrane fusion, we design a polypeptide and recombinant protein inhibiting the membrane fusion between influenza virus and a host cell, so as to interdict influenza virus from infecting a host cell.

The purpose of the invention is to provide a polypeptide or protein that inhibits the infection of influenza virus, a gene encoding the same, and a vector and cell expressing the same, such as a recombinant DNA vector, a recombinant virus vector, etc.

In particular, in the first aspect, the invention involves polypeptides HR1 and HR2 (may directly expressed as "HR1" and "HR2" hereinafter) which inhibit influenza virus from infecting host cells. The sequences of HR1 and HR2 come from conserved sequences, i.e. the 7-peptide region sequences on the envelope protein HA of the highly pathogenic avian influenza virus H5N1 (FIG. 1), wherein polypeptide HR1 represents the amino acid sequence of SEQ ID NO:1 or the sequence which is obtained by substituting and/or deleting and/or adding one or more amino acid residues of the amino acid sequence of SEQ ID NO:1 and has a function of inhibiting influenza virus infection (such as SEQ ID NO:2 and SEQ ID NO:3); polypeptide HR2 represents the amino acid sequence of SEQ ID NO:4 or the sequence which is obtained by substituting and/or deleting and/or adding one or more amino acid residues of the amino acid sequence of SEQ ID NO:4 and has a function of inhibiting influenza virus infection (such as SEQ ID NO:5).

The above substitution and/or deletion and/or addition of one or more amino acid residues involve the addition and/or deletion at any position within the sequence and/or at the two terminals thereof. Among others, those are preferably varied into the amino acids which have the side chains with similar features as the original amino acid residues, so as to preserve the original function and activity. The amino acids with similar features include, respectively, hydrophobic amino acids (A, I, L, M, F, P, W, Y, V), hydrophilic amino acids (R, D, N, C, E, Q, G, H, K, S, T), amino acids with aliphatic side chains (G, A, V, L, I, P), amino acids with side chains of hydroxyl (S, T, Y), amino acids with side chains of sulfur atom (C, M), amino acids with side chains of carboxyl and amide (D, N, E, Q), amino acids with side chains of basic group (R, K, H), and amino acids with aromatic side chains (H, F, Y, W).

In the second aspect, the invention relates to a protein obtained by connecting sequence HR1 and sequence HR2 via linking peptides (i.e. linker 1 and linker 2), wherein the linker 1 and linker 2 independently are linking peptides, respectively. In this invention, each active component (such as HR1, HR2) can be connected via linking peptides, or directly connected without any linking peptide or directly mixed. Preferably, the invention relates to a recombinant peptide, HR12121, obtained by connecting sequence HR1 and sequence HR2 via linking peptides (i.e. linker 1 and linker 2) (The schematic diagram of such protein is shown in FIG. 2).

In the currently invention, said linking peptides linker 1 and linker 2 are the sequences well known in this field, comprising at least one of glycine, serine, proline, and alanine. For instance, the linking peptide may be a polypeptide consisted of 1-50 amino acids, comprising several glycine and/or serine and/or proline and/or alanine residues combined in any way, and having a representative sequence shown in SEQ ID NO:6-10, respectively.

The arrangement order of the above 5-helix protein is NH2HR1-Linker1-HR2-linker2-HR1-Linker1-HR2-linker2-HR1COOH; with a representative sequence shown in SED ID NO:11.

The invention also relates to a derivative of the polypeptide or protein described above, for example, a recombinant protein formed by fusing with a tag for protein detection and purification, (including but not limiting to) such as enhanced green fluorescent protein (EGFP), histidine tag ($His_6$), glutathione S-transferase (GST), maltose binding protein (MBP), N-site-utilizing protein (Nus), etc. The invention also involves a mixture formed by combining the above one or more polypeptides and proteins.

In the third aspect, the invention relates to a DNA sequence encoding the above polypeptide or protein with a function of inhibiting influenza virus infection. In particular, the DNA sequence encoding polypeptide HR1 is selected from any of the following polynucleotide sequences: 1) the polynucleotide sequence of SEQ ID NO:12; 2) a polynucleotide sequence encoding the amino acid sequence of SEQ ID NO:1; 3) a polynucleotide sequence hybridized with the polynucleotide sequence of SEQ ID NO:12 under a highly stringent condition, which also encoding a polypeptide with an activity of inhibiting influenza virus from infecting host cells; 4) a polynucleotide sequence possessing a homology of 90% and more, preferable 95%, 96%, 97%, 98% or 99% with the polynucleotide sequence of SEQ ID NO:12 and encoding a protein with an activity of inhibiting influenza virus from infecting host cells. The DNA sequence encoding polypeptide HR2 is selected from any of the following polynucleotide sequences: 1) the polynucleotide sequence of SEQ ID NO:13; 2) a polynucleotide sequence encoding the amino acid sequence of SEQ ID NO:4; 3) a polynucleotide sequence hybridized with the polynucleotide sequence of SEQ ID NO:13 under a highly stringent condition, which also encoding a polypeptide with an activity of inhibiting influenza virus from infecting host cells; 4) a polynucleotide sequence possessing a homology of 90% and more, preferable 95%, 96%, 97%, 98% or 99% with the polynucleotide sequence of SEQ ID NO:13 and encoding a protein with an activity of inhibiting influenza virus from infecting host cells.

In the fourth aspect of the invention, there provides a polynucleotide sequence encoding protein HR12121, which is selected from any of the following polynucleotide sequences: 1) the polynucleotide sequence of SEQ ID NO:14; 2) a polynucleotide sequence encoding the amino acid sequence of SEQ ID NO:11; 3) a polynucleotide sequence hybridized with the polynucleotide sequence of SEQ ID NO:14 under a highly stringent condition, which also encoding a protein with an activity of inhibiting influenza virus from infecting host cells; 4) a polynucleotide sequence possessing a homology of 90% and more, preferable 95%, 96%, 97%, 98% or 99% with the polynucleotide sequence of SEQ ID NO:14 and encoding a protein with an activity of inhibiting influenza virus from infecting host cells.

Said "hybridized under a highly stringent condition" means the nucleic acids can be hybridized under a condition described in Maniatis T. et al. (ed.), Molecular Cloning: A Laboratory Manual $2^{nd}$ ed., Cold Spring Harbor Laboratory (1989) or a similar condition thereof. For instance, it indicates an hybridization ability under the following condition: 1) The double-strand molecules in the polynucleotide molecules shown in SEQ ID NO:12, 13 or 14 are denatured after a treatment of acid, base, or heat. The denatured molecules are then fixed onto a nitrocellulose membrane, a nylon membrane or other solid phase matrix capable of binding single-strand DNA molecules. After denaturation, a hybridization solution containing an exogenous polynucleotide of specified sequence is added. Hybridization is performed at 68° C. for 4-20 h. If a double strand is formed between the exogenous polynucleotide molecule and the polynucleotide molecule fixed on the membrane, then it means that these two molecules are able to hybridize. 2) The polynucleotide molecules shown in SEQ ID NO:12, 13 or 14 are added into a hybridization solution. After denaturation, an exogenous polynucleotide is also added and hybridization is performed at 68° C. for 4-20 h. The double strand formed after hybridization may be specifically adsorbed onto hydroxyapatite or other matrixes capable of binding to double-strand DNA molecules. The hydroxyapatite or matrixes adsorbing double-strand nucleic acid molecules can be collected by centrifugation, thus obtaining the hybridized double-strand DNA molecules. In this case, it is also indicated that the exogenous polynucleotide molecule can be hybridized with the sequences of the invention.

The fifth aspect of the invention relates to a vector comprising the polynucleotide sequence described above. Such a vector may include a conventional bacterial plasmid, cosmid, phagemid, yeast plasmid, plant virus, animal virus, and any other viral vectors commonly used in the art. The vectors suitable for the invention include but are not limited to vectors used for expressing in bacteria (including all types of prokaryotic expression vectors), vectors used for expressing in yeast (such as the vectors of *Pichia pastoris* and *Hansenula polymorpha*, etc), baculovirus vectors used for expressing in insect cells, vectors used for expressing in mammals (such as adenovirus vector, vaccinia virus vector, retrovirus vector, lentivirus vector, etc.), plant virus vectors used for expressing in plants and organ-specific expression vectors used in mammals, such as mammary expression vectors, etc. In conclusion, any plasmid or vector may be used as long as they can be stably replicated and passaged in host cells. Preferred expression vectors include selective marker gene, such as anti-ampicillin gene, anti-acheomycin gene, anti-kanamycin gene, anti-streptomycin gene, anti-chloramphenicol gene, etc for bacterial; anti-neomycin gene, anti-Zeocin gene for microzyme; defection selective markers, such as His, Leu, Trp, etc for microzyme; anti-neomycin gene, anti-Zeocin gene, dihydrofolacin reductase gene and fluorescin marker gene, etc for enkaryoctye. Those skilled in the art are able to create the expression vectors comprising the specific elements such as DNA sequences, suitable transcription and translation sequences, promoters and selective marker genes, etc described in the invention using a series of techniques including the DNA recombination technique known in the art. The above vectors can be used to transform and transfect appropriate host cells or organisms, thereby obtaining the desired protein of interest.

The sixth aspect of the invention also provides a cell comprising the vector described above. Such a cell may be a prokaryotic cell or an eukaryotic cell, such as a bacterial cell, a yeast cell, a plant cell, an insect cell, a mammal cell, etc. After transformed or transfected with the inventive DNA sequence encoding a polypeptide or protein with a function of inhibiting influenza virus infection, the host cells may be used for producing the desired polypeptide and protein, or for administering directly.

Those skilled in the field are able to properly select the suitable vectors and host cells, and know how to efficiently transform or transfect cells with those vectors. The used methods include but are not limited to the calcium chloride method and electroporation method for bacterial cells; the electroporation method and protoplast fusion method for yeast cells; liposome packaging, calcium phosphate co-precipitation, electronfusion method and microinjection method, etc for eukaryotic cells such as mammal cells etc.

In the seventh aspect of the invention, there provides a medicine used for treating influenza virus infection, comprising a therapeutic effective amount of polypeptide according to the first aspect and/or protein according to the second aspect and/or a vector or cell comprising the polynucleotide according to the third and/or fourth aspects.

The inventive medicine may be prepared into an injection solution, tablet or spray based on conventional methods in the pharmaceutical field. One or more pharmaceutical acceptable carriers may also be added to the above medicine, if needed. Such carriers include conventional diluters, excipients, fillers, binders, humectants, disintegrants, absorbing promoters, surfactants, adsorption carriers, and lubricants, etc in the pharmaceutical field. Flavors and sweeteners, etc. may be added as well when necessary.

In the eighth aspect of the invention, there provides a method for treating influenza virus infection, comprising administering a therapeutic effective amount of polypeptide according to the first aspect, protein according to the second aspect, a vector or cell comprising the polynucleotide according to the third and fourth aspects to a subject. Also, the method comprises the step of administering a therapeutic effective amount of combination of one or more polypeptides, proteins, vectors, or cells described above to a subject.

The administration may be carried out via a route well known by those skilled in the art, such as injection, oral, pulmonary, nasal, buccal administration, etc. Preferable routes are pulmonary, nasal, and buccal administration. The dose may vary according to the dosage form, the expected functioning time and the status of the subject being treated. The actual amount required for the treatment (i.e. the effective dose) may be readily determined by a physician in accordance with actual status (such as the condition, age and weight etc of the subject). Regarding the administration by injection, preferable dosage is 100 ng-10 mg/kg body weight, more preferably 1 μg-1 mg/kg body weight, and most preferably 10 μg-100 μg/kg body weight.

In the ninth aspect of the invention, there provides a kit for treating influenza virus infection, comprising: 1) the polypeptide according to the first aspect or the protein according to the second aspect, or a vector or cell comprising the polynucleotide according to the third and fourth aspects, or a combination of one or more polypeptides, proteins, vectors, or cells described above; 2) an instruction indicating the administration modes, including the order, time, dosage and route, etc. of administration.

The tenth aspect of the invention relates to the use of the polypeptide according to the first aspect or the protein according to the second aspect or a vector or cell comprising the polynucleotide according to the third and fourth aspects or a mixture comprising a combination of one or more polypeptides, proteins, vectors, or cells described above for preparing medicines used for treating influenza virus infection.

The inventive method may be used for treating influenza virus infection, especially the infection of influenza virus H5N1, H1N1 and/or H3N2, preferably of the highly pathogenic avian influenza virus (H5N1), and most preferably of a Qinghai strain of the highly pathogenic avian influenza virus H5N1 isolated in China.

The polypeptide according to the first aspect or the protein according to the second aspect or a vector or cell comprising the polynucleotide according to the third and fourth aspects or a combination of one or more polypeptides, proteins, vectors, or cells described above are preferably used for human, mammals, or avian.

In order to be understood, the invention will be described in detail with reference to particular Figures and examples hereinafter. It is noted that this description is only for an illustration purpose, but not intended to limit the scope of the invention. According to the description, the advantageous effect of the invention is obvious to those skilled in the art. In addition, some published references with a function of more clearly describing the invention are cited in the description, which are incorporated as a whole by reference, just like the entirety of which have been recited herein.

DETAILED DESCRIPTION OF THE PREFERRED EMBODIMENT

Figure 1:
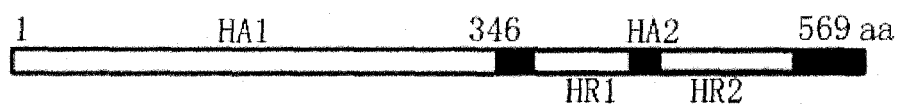
FIG. 1: The primary structure of membrane protein HA of avian influenza virus involved in the invention. After synthesized, HA protein may be digested into two subunits, HA1 (at 1-346 amino acid positions) and HA2 (at 347-569 amino acid positions), by a specific protease. This Figure shows the position of 7-peptide repeat regions, HR1 and HR2 in HA2 subunit.
Figure 2:
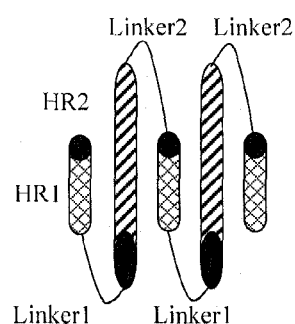
FIG. 2: The schematic structural diagram of the recombinant protein HR12121 in the invention. HR1 and HR2 are connected via specific linking peptides, Linker1 and Linker2, wherein Linker1 and Linker2 may be same or different, and sequences of the linking peptides are shown in SEQ ID NO:6-10, respectively.

The present invention is further explained and illustrated by the following examples. It is appreciated by those skilled in the art that the only purpose of the following examples is to illustrate, and the spirit and scope of the invention is defined by the attached claims. The invention may be performed according to any method listed in laboratory manuals well known by those skilled in the art such as Molecular Cloning A Laboratory Manual ($3^{rd}$ ed.) (Science Press, Beijing, China, 2002), Cell A Laboratory Manual (Science Press, Beijing, China, 2001) etc. and the references cited herein, unless otherwise indicated. In the following examples, all the percentages are mass percentages, unless otherwise indicated. The used solution formulations are described in Molecular Cloning A Laboratory Manual, unless otherwise indicated. All the operations for living influenza virus involved in the invention are conducted in Laboratory BSL-3 of the Key Laboratory of Pathogenic Organism in Chinese Academy of Military Medical Science.

Example 1

Construction of the Viral RNA Expression Vectors for HA and NA Genes of the Highly Pathogenic Avian Influenza Virus Strain A/Bar-headed Goose/Qinghai/1/05

1.1) Extraction of Viral RNA

The highly pathogenic avian influenza virus strain A/bar-headed goose/Qinghai/1/05 (shortened as strain "QH" hereinafter) is the highly pathogenic avian influenza virus $H_5N_1$, which was isolated and stored in our lab (see Liu et al, 2005). The allantoic fluid of chicken embryo containing influenza virus strain QH stored at −70° C. was centrifuged at 3000 r/m for 10 min to remove protein impurities. Subsequently, 140 μl of supernatant was pipetted into a 1.5 ml RNase-free centrifuge tube. Viral RNA was extracted using a virus RNA extraction kit (QIAmp Viral RNA Mini Kit, CAT. No. 52904), according to the instruction of the manufacture. After extraction, adsorption, wash, centrifuge, and elution, 60 μl of viral RNA solution was obtained, and then packed in aliquots and stored at −80° C.

1.2) RT-PCR Amplification of HA and NA Gene Fragments of Strain QH (1) Design, Synthesis of Primers and RT (Reverse Transcription) Reaction According to the sequencing results obtained by Liu et al. (2005), the following primers were designed in order to perform a RT-PCR reaction:

```
P1: GCAAAAGCAGGGGTCTGATCTGTC              (SEQ ID NO: 15)

P2: AGTAGAAACAAGGGTGTTTTTAACTAC           (SEQ ID NO: 16)

P3: GCAAAAGCAGGAGTTCAAAATG                (SEQ ID NO: 17)

P4: AGTAGAAACAAGGAGTTTTTTGAACAGACTACTTG   (SEQ ID NO: 18)
```

The kit used in RT-PCR reaction was TaKaRa RNA PCR Kit (AMV) Ver. 3.0 (Code No. DRRO19A). The RT reaction system of HA gene was shown as follows: $MgCl_2$, 2 μl; 10×RT Buffer: 1 μl; RNase Free $dH_2O$: 1.75 μl; dNTPs (each 10 mM): 1 μl; RNase Inhibitor: 0.25 μl; AMV Reverse Transcriptase: 0.5 μl; primer P1: 0.5 μl; viral genomic RNA templet: 3 μl, in total 10 μl. Reaction condition was: incubation at 30° C. for 10 min, extension at 42° C. for 30 min, inactivation at 99° C. for 5 min, and ice bathing at 0° C. for 5 min. The RT reaction system and the reaction condition for NA gene were same as those of HA gene, except that primer P3 was used instead of P1.

(2) PCR Amplification

The PCR reaction system (50 μl) of HA gene (SEQ ID NO:37) was shown as follows: 5×PCR Buffer: 10 μl; sterilized DEPC water: 28.75 μl; TaKaRa Ex Taq HS: 0.25 μl; primers P1 and P2 (10 μM): 0.5 μl each; RT product: 10 μl. Reaction condition was: pre-denaturalization at 94° C. for 2 min; 30 cycles of denaturalization at 94° C. for 30 sec, anneal at 55° C. for 30 sec, extension at 72° C. for 2 min; and then final extension at 72° C. for 10 min. The PCR reaction system and the reaction condition for NA gene (SEQ ID NO:48) were same as those of HA gene, except that primers P3 and P4 were used instead of primers P1 and P2. The PCR product was ligated into pGEM-T vector (Promega Inc.) after cutted and purified from gel (with a gel recovering kit, i.e. QIAquick Gel Extraction Kit (250), CAT. No. 28706), respectively. The ligation system was shown as follows: PCR product: 7 μl; pGEM-T vector: 1 μl; 10×ligase buffer: 1 μl; T4 DNA ligase: 1 μl. After ligation at 16° C. for 12 hours or long, the ligated product was used to transform E. coli competent DH5α cells (prepared and stored in our lab). The positive clones were identified by sequencing, designated as pGEM-HA and pGEM-NA, respectively.

1.3) Targeting Cloning of HA and NA Gene Fragments of Influenza Virus Strain QH into Plasmid pHH21

Figure 3:
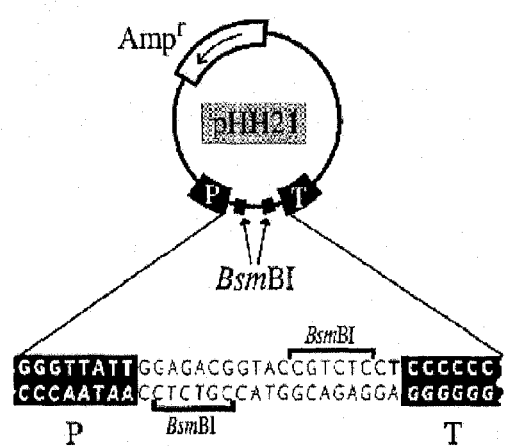
FIG. 3: The restriction map and restriction sites of the RNA expression vector pHH21 of influenza virus. P: the promoter site of human RNA polymerase; T: the terminator of mouse RNA polymerase I; BsmBI: the restriction site on the vector, used for cloning exogenous genes, Amp$^r$: anti-ampiciline gene, used as a screening marker.

In order to prepare recombinant virus by a reverse genetic system of influenza virus, viral RNA expression vector pHH21 (with a map shown in FIG. 3) was commonly used to express genomic negative-strand RNA of influenza virus. For a purpose of targeting cloning of HA and NA gene fragments into plasmid pHH21 (gifted from Prof. Yoshihiro Kawaoka in University of Wisconsin, USA, see Neumann et al, 1999), the following primers were designed and synthesized:

```
P5: ATATCGTCTCGTATTAGTAGAAACAAGG    (SEQ ID NO: 19)

P6: TATTCGTCTCGGGGAGCAAAAGCAGGGG    (SEQ ID NO: 20)
```

HA and NA gene fragments were amplified from the templet i.e. pGEM-HA and pGEM-NA respectively, using the PCR system (25 μl) shown as follows: 5×PCR Buffer: 5 μl; sterile water: 12.8 μl; dNTPs (10 mM each): 4 TaKaRa Ex Taq HS: 0.2 μl; primers P5 and P6 (10 μM):1 μl each; plasmid templet: 1 μl. Reaction condition was: pre-denaturalization at 94° C. for 2 min; 30 cycles of denaturalization at 94° C. for 30 sec, anneal at 56° C. for 30 sec, extension at 72° C. for 2 min; and then final extension at 72° C. for 10 min. The fragment of interest was digested with BsmBI (New England Biolabs) at 55° C. for 8 h, after purified by gel cutting and recovering, wherein the reaction system was shown as follows: PCR product: 15.0 μl; 10×NEB buffer 3: 5 μl; sterile water: 28 μl; BsmBI enzyme: 2 μl. After cutted and purified from the gel, the fragment of interest was ligated to pHH21 vector digested with the same enzyme, wherein the reaction system was shown as follows: PCR product: 10 μl; pHH21 vector: 6 μl; 10× ligase buffer: 2 μl; T4 DNA ligase: 2 μl. After ligation at 16° C. for 12 hours or long, the ligated product was used to transform E. coli competent DH5α cells. The positive clones were identified by sequencing, designated as pHH21-HA (QH) and pHH21-NA (QH), respectively.

Example 2

Preparation of Recombinant Influenza Virus WSN and QH-WSN 2.1) Preparation of Recombinant Influenza Virus WSN The recombinant human influenza virus A/WSN/33 (H1N1 subtype, sometimes shortened as "WSN" hereinafter) was prepared using a reverse genetic system of influenza virus with 12 plasmids (Luytjes et al, 1989). The reverse genetic system with 12 plasmids was gifted from Prof. Yoshihiro Kawaoka in University of Wisconsin, USA (Neumann et al; 1999). Such system comprises the expression plasmids for expressing 8 negative-strand RNA fragments in influenza virus genome (including pHH21-PB2, pHH21-PB1, pHH21-PA, pHH21-HA, pHH21-NP, pHH21-NA, pHH21-M and pHH21-NS) and 4 protein expression plasmids for expressing replicase complex of influenza virus (including pcDNA3-PB2, pcDNA3-PB1, pcDNA3-PA and pCAGGS-NP). E. coli competent DH5α cells were transformed with the above plasmids respectively. A single clone was picked and cultured in LB medium for 6 hours or long. Plasmids were extracted using QIAprep Spin Miniprep Kit (250) (CAT. No. 27106). The 12 plasmids described above were mixed in equal amounts and used for transfect 293T cells (purchased from American Type Culture Collection, ATCC number: CRL-11268) by the calcium phosphate method (see Molecular Cloning A Laboratory Manual). Ten hours later, fresh Dulbecco's modified Eagle's medium (DMEM) (Gibco Inc.) was used. After cultured at 37° C. for 72 h, the cell culture supernatant was used to infect MDCK cells (Madin-Darby canine kidney cell, purchased from China Center for Type Culture Collection, CCTCC number: GDC012). Cell lesion appeared 3-4 days later. The supernatant was harvested, diluted for 1000 times, and used for inoculating allantoic cavities of 9-day chicken embryos at 37° C. for 2-3 days. Allantoic fluid was harvested following the death of the chicken embryos, and packed in aliquots after centrifuging, followed by storage at −70° C. As a result, the recombinant human influenza virus A/WSN/33 was obtained, which was shortened as "WSN" hereinafter.

2.2) Preparation of Recombinant Influenza Virus QH-WSN

In accordance with the above, the above reverse genetic system with 12 plasmids was used, wherein two plasmids pHH21-HA and pHH21-NA were replaced by plasmids pHH2'-HA (QH) and pHH21-NA (QH) of strain QH prepared as above. In other words, the recombinantly hybridized virus, designated as "QH-WSN", was prepared using the above reverse genetic system, in which HA and NA genes of WSN had been replaced by HA and NA genes of strain QH. HA and NA protein of QH-WSN come from the highly pathogenic avian H5N1 influenza virus. Therefore, QH-WSN belongs to H5N1 subtype too, and possesses an infection feature of the highly pathogenic avian influenza virus.

Example 3

Plaque Potency Test of Experimental Influenza Virus

In order to test inhibitory effect of the inventive polypeptide and protein on the highly pathogenic avian influenza virus, we detected their inhibitory effect on recombinant virus QH-WSN possessing an infectious feature of the highly pathogenic avian H5N1 influenza virus. On the other hand, for the purpose of testing whether the above polypeptide and protein have a crossing inhibitory effect on human influenza virus, we detected their inhibitory effect on recombinant virus WSN (human influenza virus) which has a similar genetic background with QH-WSN but possesses a H1N1 subtype surface membrane protein. In addition, we also detected their crossing inhibitory effect on a representative strain (A/Jiangxi/312/2005; shortened as strain "JX") of human H3N2 influenza virus isolated from the southern China in 2005 (Lanyu et al., 2006).

Since a canine kidney passage cell (MDCK) is a sensitive cell strain suitable for growing influenza virus (Gaush et al, 1966), it was used for detecting infectivity of influenza virus in the invention. The used detailed method was the plaque inhibition experiment. In this experiment, plaque potency is required to be determined. Therefore, plaque potency of 3 original viral solutions, i.e. WSN, QH-WSN and JX, was first detected by the plaque experiment, respectively.

MDCK cells were inoculated into a 12-well cell culture plate, and cultured for 24-36 hours in an incubator at 37° C. (5% $CO_2$). The supernatant was discharged after 100% confluent growth of the cells. The cells was washed 2× with PBS solution (pH 7.4), and washed 1× with serum-free DMEM medium (Because fetal calf serum inhibits infection of host cells with influenza virus, the cells need to be washed before added to virus, so as to remove the residual serum in the medium). The 3 of above original viral solutions were serially diluted in a 10× gradient, respectively. Into each well of cells, 500 µl of the dilution was added, with 3 replications for each gradient. The viral solution was discharged after cultured at 37° C. for 1 h. The cells were washed with 2× with PBS, and then washed 1× with serum-free DMEM medium, so as to remove virions which were not adsorbed. Agarose (3%) with a low-melting point was pre-melted and maintained until reaching room temperature. Six milliliter of the agarose was added into equal amounts of serum-free DMEM medium (no phenol red, no color, purchased from Gibco Inc.) pre-heated to 37° C. and 1× trypsin (300:1; purchased from Gibco Inc.). The mixture was added into wells, 1 ml/well, after mixed thoroughly. Agarose was solidified after being kept at room temperature in an upside position for 30 min or longer, followed by being cultured with an upside-down position in an incubator at 37° C. for 2-4 days. Once plaques appeared and diffused to a size suitable for observation, an appropriate amount of melted agarose (3%) with a low-melting point was taken and kept at room temperature. Equal amounts of serum-free DMEM medium (no phenol red, no color) pre-heated to 37° C. and 1% neutral red (20:1; purchased from Gibco Inc.) were added to the agarose and mixed thoroughly. The resultant mixture was added into wells, 1 ml/well. The agarose was solidified after being kept at room temperature in an upside position for 30 min or longer, followed by being cultured with an upside-down position in an incubator at 37° C. for 1-2 days. Once plaques became clear, their number was counted. Each well was counted for at least twice, in order to avoid error. Each group of experiments was performed in triplicate at least. The plaque potency of the original viral solutions was calculated in accordance with the number of plaques and the dilution factor of virus. The result of plaque potency was $10^{6.3}$ PFU/ml (PFU is the abbreviation of plaque formation unit) for WSN; $10^{4.5}$ PFU/ml for QH-WSN; and $10^{5.2}$ PFU/ml for JX.

Example 4

Chemical Synthesis of Polypeptide HR1 Derived from Strain QH and Detection of its Activity of Inhibiting Viral Infection 1) Chemical Synthesis of Polypeptide HR1

According to the amino acid sequence of SEQ ID NO:1 in Sequence Listing, polypeptide HR1 (21 amino acids in length) derived from strain QH was synthesized with a purity of more than 95% using a chemical synthesis method. The resultant polypeptide HR1 was purified by HPLC, identified by mass spectrum (Beijing SciLight Biotechnology Ltd. Co.), dissolved with sterile PBS solution (pH 7.4) to provide a final concentration of 2 mM, stored at 4° C., and used within a week.

2) Detection of the Activity of Polypeptide HR1 for Inhibiting 3 Types of Influenza Virus Infection MDCK cells were inoculated and cultured as performed in Example 3. Polypeptide HR1 solution was serially diluted with serum-free DMEM medium into concentrations of 200, 20 and 2 µM, respectively. On the other hand, the 3 types of influenza virus were diluted with serum-free DMEM medium into a concentration of 160 PFU/ml according to their respective PFU potency, and mixed with an equal amount of the above serially diluted solution of polypeptide HR1. In this case, the final concentrations of the polypeptide were 100, 10 and 1 µM; whereas the final concentration of the virus was 80

PFU/ml. The medium was discharged from the wells, and 500 μl of the above mixture was added into each well, i.e. PFU of virus/well, 4 groups in total. One of these groups was the viral control only added with virus but no polypeptide added; and the rest 3 groups were experimental groups with serially diluted polypeptide+virus. There were 3 replicated wells in each group. The cells were infected at 37° C. for 1 h after the addition of a suspension of virus. Subsequently the supernatant was discharged, and the cells were washed 2× with PBS and 1× with serum-free DMEM medium, so as to remove the virions which were not adsorbed. The following procedures of the plaque experiment were same as those in the experiment for detecting plaque potency.

The result was read in accordance with the following criteria: normal cell status, no death and no plaque in the cell control group; a large amount of plaques in the virus control group. The numbers of plaques were counted in the experimental groups. The plaque inhibitory rate, at each polypeptide concentration, was calculated according to the following formula: Inhibitory rate (%)=(number of plaques in the virus control group−number of plaques in the experimental group)/number of plaques in the virus control group×100%. After calculation of the plaque inhibitory rate at each polypeptide concentration, 50% inhibiting concentration ($IC_{50}$) or inhibition percentage at a specific concentration were calculated in accordance with Karber method. Each group of experiments was performed in triplicate.

Figure 4:
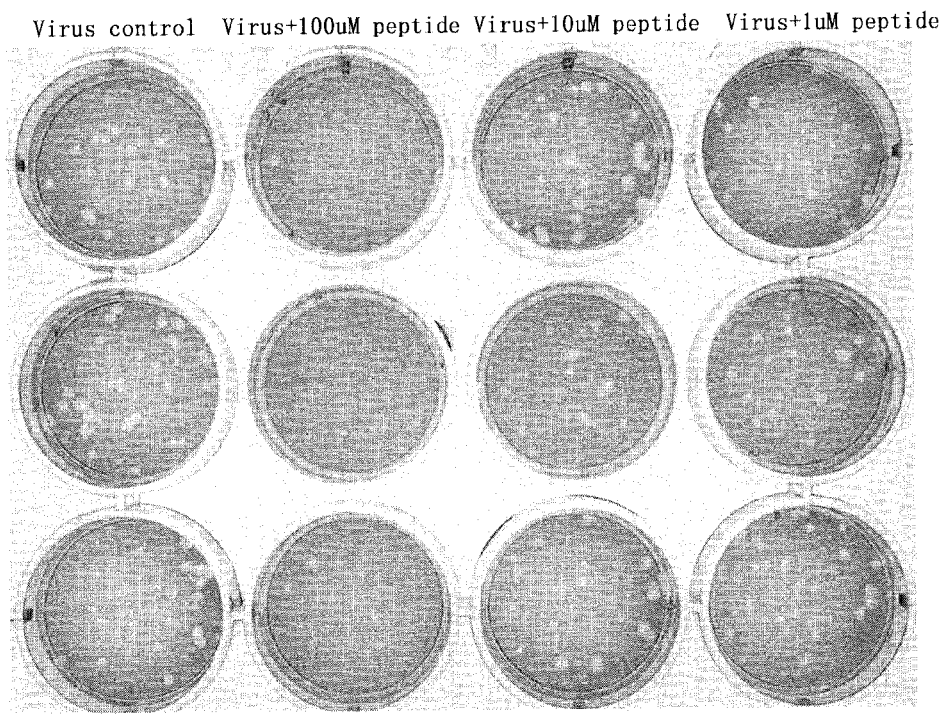
FIG. 4: Inhibitory effect of polypeptide HR1 synthesized chemically in the invention on plaques of QH-WSN avian influenza virus. Virus control: the plaque control generated after infection of cells with only virus but not polypeptide; virus+peptide: the plaque generated after infection of cells with a mixture of virus and polypeptide HR1 at different concentration (The final concentration of the polypeptide is 100, 10 and 1 μM, respectively). This Figure shows that the white dot in each well is the plaque generated by diffusion of avian influenza virus into adjacent cells after infecting a single cell. After stained with neutral red (0.05%), living cells can be stained and thus display a red color; whereas the cells infected with virus can not be stained and thus display a white color since they have been died already.

The inhibitory effect of polypeptide HR1 at different concentration on formation of plaques of QH-WSN avian influenza virus was shown in FIG. 4. The inhibitory effect of polypeptide HR1 at different concentration on formation of plaques of WSN (an H1N1 subtype) and JX (an H3N2 subtype) was similar with that shown in FIG. 4, so that its Figure was elided. A statistic result indicated that $IC_{50}$ of polypeptide HR1 was 15.8±2.3 μM for QH-WSN virus (avian influenza virus H5N1); 11.1±3.8 μM for WSN virus (human influenza virus H1N1); and 16.4±2.5 μM for JX virus (human influenza virus H3N2).

In conclusion, the above results demonstrated that 1) polypeptide HR1 derived from the protein HA2 of avian influenza virus strain QH (an H5N1 subtype) at a micromole concentration level could effectively inhibit the infection of host cells with avian influenza virus strain QH-WSN; 2) polypeptide HR1 derived from avian influenza virus strain QH could not only inhibit the infection of host cells with homologous avian influenza virus strain QH (an H5N1 subtype), but also effectively inhibit the infection of host cells with various subtypes of human influenza virus (H1N1 subtype and H3N2 subtype). A segment of polypeptide (the amino acid sequence of KLPDDFMGCV) derived from membrane protein S of SARS virus was used as a control of unrelated peptide segments. The result showed that such peptide, at a final concentration of 400 μM, did not inhibit the infection of influenza virus, which indicating that inhibition of infection of avian and human influenza virus by the polypeptide HR1 derived from membrane protein HA2 of avian influenza virus was specific.

Example 5

Chemical Synthesis of Mutated HR1 Polypeptides and Detection of their Inhibitory Activity 1) Chemical Synthesis of Mutant Polypeptide HR1-1 and Detection of its Inhibitory Activity In order to test whether the mutated HR1 polypeptide still possesses inhibitory activity, the amino acid A at 7 position in polypeptide HR1 sequence (SEQ ID NO:1) was substituted with I, thus providing a sequence designated as HR1-1 (SEQ ID NO:2). Polypeptide HR1-1 was synthesized chemically and dissolved by following the steps in section 1) of Example 4.

The activities of polypeptide HR1-1 for inhibiting 3 types of influenza virus were detected using the same method as section 2) of Example 4. The statistic result showed that $IC_{50}$ of polypeptide HR1-1 was 32.7±6.5 μM for QH-WSN virus (avian influenza virus H5N1); 29.3±5.7 μM for WSN virus (human influenza virus H1N1); and 38.2±7.8 μM for JX virus (human influenza virus H3N2).

2) Chemical Synthesis of Mutant Polypeptide HR1-2 and Detection of its Inhibitory Activity In order to test whether other mutated HR1 polypeptides still possess inhibitory activity, the 4 hydrophobic amino acid A were inserted after 12 position in polypeptide HR1 sequence (SEQ ID NO:1), thus providing a sequence designated as HR1-2 (SEQ ID NO:3). Polypeptide HR1-2 was synthesized chemically and dissolved by following the steps in section 1) of Example 4.

The activities of polypeptide HR1-2 for inhibiting 3 types of influenza virus were detected using the same method as section 2) of Example 4. The statistic result showed that $IC_{50}$ of polypeptide HR1-2 was 104.5±28.6 μM for QH-WSN virus (avian influenza virus H5N1); 110.2±28.2 μM for WSN virus (human influenza virus H1N1); and 111.9±19.5 μM for JX virus (human influenza virus H3N2).

In view of the above results, it was indicated that both the point mutant polypeptide HR1-1 and insertion mutant polypeptide HR1-2, at a micromole concentration level, could effectively inhibit the infection of host cells with avian influenza virus strain QH-WSN and human influenza virus strain WSN and JX. Therefore, the polypeptides formed after polypeptide HR1 had been appropriately engineered or mutated still inhibited the infection of influenza virus.

Example 6

Chemical Synthesis of Polypeptide HR2 of Avian Influenza Virus Strain QH and Detection of its Inhibitory Activity 1) Chemical Synthesis of Polypeptide HR2 of Strain QH According to the amino acid sequence of SEQ ID NO:4 in Sequence Listing, polypeptide HR2 (51 amino acids) derived from strain QH was synthesized with a purity of more than 95% using a chemical synthesis method. On the other hand, polypeptide HR2 was divided into 3 polypeptide segments overlapped one another, i.e. HR2A (20 amino acids), HR2B (23 amino acids) and HR2C (16 amino acids) which were synthesized respectively. The sequences of HR2A, HR2B and HR2C were shown as follows. The resultant polypeptides were purified by HPLC, identified by mass spectrum, and dissolved with DMEM medium to provide a solution with a relatively low final concentration of 0.4-1 mM due to the high content of hydrophobic amino acids therein. Then the solution was stored at 4□, and used within a week.

```
HR2A:  RRIENLNKKMEDGFLDVWTY      (SEQ ID NO: 21)

HR2B:  NAELLVLMENERTLDFHDSNVKN   (SEQ ID NO: 22)

HR2C:  FHDSNVKNLYDKVRLQ          (SEQ ID NO: 23)
```

2) Detection of the Activity of Polypeptide HR2 for Inhibiting Infection of Influenza Virus According to the method described in section 2) of Example 4, inhibitory effect of HR2A, HR2B, HR2C and HR2 on plaques formed on MDCK cells by influenza virus strains QH-WSN, WSN and JX was detected. Because the above polypeptides comprise a large amount of hydrophobic amino acids, they have relatively low solubility in DMEM medium and the inhibitory rate of influenza virus infection by the polypeptides with high concentrations can not be detected. In this case, the inhibitory rates of the 3 types of virus by the above 4 polypeptides with specified concentrations were detected (see Table 1). The experimental results showed that all of HR2A, HR2B, HR2C and HR2 had certain inhibitory effect on formation of influenza viral plaques.

TABLE 1

Inhibitory rates (%) of 3 influenza
virus types by the 3 polypeptides

| Virus | HR2A | HR2B | HR2C | HR2 |
|---|---|---|---|---|
| QH-WSN | 56.9* | 63.8* | 53.1* | 29.6*** |
| WSN | 42.0** | 43.0** | 29.6** | 40.3*** |
| JX | 51.4* | 15.2* | 17.1* | — |

*The concentration of the peptides was 200 μM;
**The concentration of the peptides was 100 μM;
***The concentration of the peptides was 50 μM;
—: no detection.

Example 7

Figure 5:
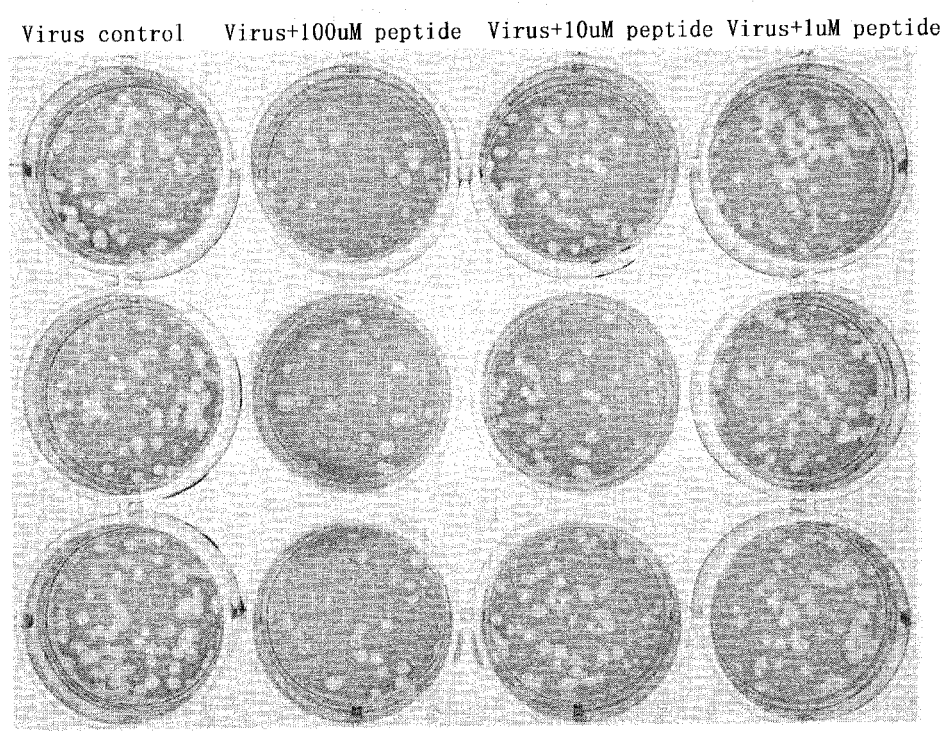
FIG. 5: Inhibitory effect on WSN influenza viral plaques after mixing of polypeptide HR1 and polypeptide HR2A synthesized chemically in the invention. Virus control: the plaque control generated after infection of cells with only virus but not polypeptide; virus+peptide: the plaque generated after infection of cells with the mixture of virus and polypeptides HR1 and HR2A at different concentration (Both of them are mixed by a ratio of 1:1. The final concentration of each polypeptide is 100, 10 and 1 μM, respectively).

Detection of the Activity of Polypeptide HR1 Respectively Combined with HR2A, HR2B or HR2C for Inhibiting Influenza Virus According to the method described in section 2) of Example 4, the inhibitory effect of polypeptide HR1 respectively combined with HR2A, HR2B or HR2C on plaques formed on MDCK cells by influenza virus strains QH-WSN and WSN was detected. The results showed that polypeptide HR1 respectively combined with HR2A, HR2B or HR2C had certain inhibitory effect on formation of influenza virus (including QH-WSN and WSN) plaques (FIG. 5). Their 50% inhibitory concentrations ($IC_{50}$) were shown in Table 2. The inhibitory effect of such combined polypeptides on JX virus was similar with the other two virus described above.

TABLE 2

Inhibitory effect of the polypeptide combinations
on influenza virus($IC_{50}$, in a unit of μM)

| Virus | HR1 + HR2A | HR1 + HR2B | HR1 + HR2C |
|---|---|---|---|
| QH-WSN | 43.6 ± 10.5 | 36.7 ± 0.4 | 41.6 ± 9.3 |
| WSN | 52.9 ± 3.2 | 62.5 ± 10.9 | 30.0 ± 0.6 |

Example 8

Inhibitory Effect of MDCK Cells Stably Expressing HR1 or HR2 Fusion Protein on Formation of Influenza Viral Plaques 1) Construction of Expression Vector pEGFP-HR1

Figure 6:
FIG. 6: The schematic structural diagram of a vector used for expressing HR1 on eukaryotic cell membrane. Signal peptide: the signal peptide of human Low-affinity Nerve Growth Factor Receptor (LNGFR) synthesized artificially; hinge: the hinge region of immunoglobulin G; membrane-spanning domain: the membrane-spanning domain of LNGFR; enhanced green fluorescent protein: the enhanced green fluorescent protein (EGFP) reporter gene on the used eukaryotic expression vector pEGFP-N1. The structure of the vector expressing HR2 on eukaryotic cell membrane is same as that of the vector expressing HR1, except for regarding HR2 instead of HR1.

We constructed an eukaryotic expression vector expressing fusion protein HR1-EGFP on cell membrane, in order to test whether the HR1 expressed on the host cell membrane was able to interfering conformation variation of membrane protein HA2 of influenza virus, and thus inhibiting the fusion between influenza virus envelope and cell membrane to inhibit the infection of host cells with influenza virus. The detailed procedures were shown as follows. The sequence (see SEQ ID NO:12) encoding HR1 of the highly pathogenic avian H5N1 influenza virus strain QH had a length of 63 bp. For a purpose of expressing HR1 on the membrane, it required to insert a protein-secreting signal peptide (SP) at N-terminal and a membrane-spanning domain (MSD) at C-terminal of HR1 protein. In the invention, the sequence encoding HR1 was fused behind the signal peptide of human low-affinity nerve growth factor receptor (LNGFR) and a hinge of immunoglobulin G and a membrane-spanning domain of LNGFR were fused at C-terminal of the sequence encoding HR1. For convenient cloning, a Kpn I digestion site was inserted at N-terminal of SP; a BamH I digestion site was inserted at N-terminal of HR1; a EcoR I digestion site was inserted at C-terminal of HR1; and a Xho I digestion site was inserted at C-terminal of MSD. Kozak sequence was an eukaryotic expression enhancing element. The schematic structural diagram of the fusion protein was shown in FIG. 6.

The following shows the schematic diagram of synthesized sequence:

Protective base-Kpn I-Kozak-SP-BamH I-HR1-EcoR I-Hinge-MSD-Xho I-protective base The complete DNA sequence encoding the above protein is shown in SEQ ID NO:24. To synthesize the sequence described above, the following 8 primers were synthesized:

```
                                         (SEQ ID NO: 25)
P7:  GGGGTACCACCATGGGGGCAGGTGCCACCGGCCGCGCCATGGACGG

GCCGCG (SEQ ID NO: 26)
P8:  CAAGGGACACCCCCAGAAGCAGCAACAGCAGCAGGCGCGGCCCGTC

CATGG (SEQ ID NO: 27)
P9:  CTGGGGGTGTCCCTTGGAGGTGCCGGATCCAAAGAATCCACTCAAA

AGGC (SEQ ID NO: 28)
P10: CAATGATCGAGTTGACCTTATTGGTGACTCCATCTATTGCTTTT

GAGTGGAT (SEQ ID NO: 29)
P11: GTCAACTCGATCATTGACAAAGAATTCGTGCCCAGGGATTGTGGT

TGTAAGCC (SEQ ID NO: 30)
P12: GGATGGAGCAATAGACGGGATGAGTGTACATATGCAAGGCTTAC

AACCACAAT (SEQ ID NO: 31)
P13: GTCTATTGCTCCATCCTGGCTGCTGTGGTGGTGGGCCTTGTGGCC

TACATAGCC (SEQ ID NO: 32)
P14: CCGCTCGAGCAGGATGCCCCTGTTCCACCTCTTGAAGGCTATGTA

GGCCACA
```

The fragments of interest were amplified by overlapping extension PCR while the above 8 primers were matched each other. The PCR system (50 μl) comprised as follows, $H_2O$:

25.8 µl; 10×pfu buffer: 5 µl; dNTPs: 4 µl; P7 and P14 (10 µM): each 2 µl; P8 and P13 (10 µM):1.6 µl each; P9 and P12 (10 µM):1.2 µl each; P10 and P11 (10 µM):0.8 µl each; pfu Taq enzyme: 4 µl. Reaction procedure included: one cycle of denaturalization at 94° C. for 4 min; 32 cycles of 94° C. for 30 s, 64° C. for 30 s, 72° C. for 30 s; and then final extension at 72° C. for 10 min. A fragment of 308 bp (see SEQ ID NO:24) was obtained and digested with Kpn I and Xho I after cutted and purified from gel. The digestion system comprised PCR product: 15 µl; 10× buffer L: 4 µl; Kpn I and Xho I enzymes (TaKaRa): 2 µl each; H₂O: 27 µl. The digestion was carried out for 8 h or longer followed by recovering of the digested fragment. The resultant fragment was ligated to an eukaryotic expression vector pcDNA4.0 (Novagen) digested with the same enzymes, wherein the reaction system was shown as follows: recovered fragment of interest: 8 µl; recovered vector framework fragment: 4 µl; 10× T4 ligase buffer: 1.5 µl; T4 ligase: 1.5 µl. After ligation at 16° C. for 10 hours or long, the ligated product was used to transform *E. coli* competent DH5α cells. The positive clones were screened, and the ones with a completely correct sequence were identified by sequencing and designated as pcDNA-HR1. However the digestion sites at both terminals of the fragment of interest did not match that of eukaryotic expression vector pEGFP-N1 (Clontech Laboratories; Inc.), so the digestion site at both terminals were re-designed as Bgl II and Pst I respectively, and the following primers were synthesized:

```
P15: CGAGATCTACCACCATGGGGGCAGGTG    (SEQ ID NO: 33)
P16: TGCACTGCAGCAGGATGCCCCTGTTCCAC  (SEQ ID NO: 34)
```

Figure 7:
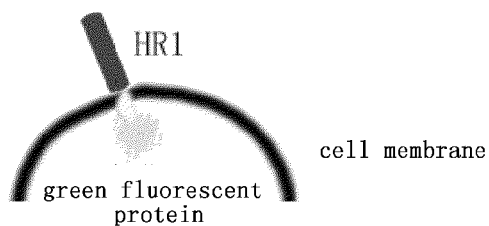
FIG. 7: The schematic diagram of expression of HR1 on eukaryotic cell membrane. HR1 is expressed outside the membrane and anchored on the membrane with a membrane-spanning domain. EGFP is expressed inside the cell membrane and does not impact HR1 function, thus providing a marker for screening stably cloned cell lines. The schematic diagram of expression of HR2 on eukaryotic cell membrane is similar as that of HR1, except for regarding HR2 instead of HR1.
Figures 8A, 8B:
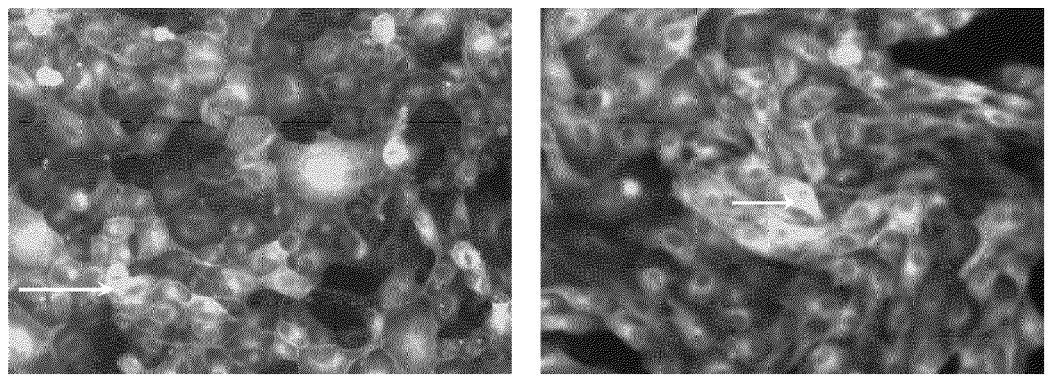
FIG. 8A: MDCK cells stably expressing the fusion protein HR1-EGFP. The fusion protein HR1-EGFP displays a green color under a fluorescent microscope after excited by a blue light. This Figure shows that the fusion protein HR1-EGFP is expressed both inside the cells and on the surface of the cell membrane. The arrow only shows one of them.
FIG. 8B: MDCK cells stably expressing the fusion protein HR2-EGFP. The fusion protein HR2-EGFP displays a green color under a fluorescent microscope after excited by a blue light. This Figure shows that the fusion protein HR2-EGFP is expressed both inside the cells and on the surface of the cell membrane. The arrow only shows one of them.

The fragment of interest with Bgl II and Pst I digestion sites at each terminal respectively was obtained by PCR. The used PCR system comprised H₂O: 16 µl; 10×pfu buffer: 2.5 µl; dNTPs: 2.5 µl; P15 and P16 (10 µM): 1 µl each; templet pcDNA-HR1: 1 µl; pfu Taq enzyme: 1 µl. Reaction procedure included: one cycle of 94° C. for 4 min; 32 cycles of 94° C. for 30 s, 64° C. for 30 s, and 72° C. for 30 s; and then final extension at 72° C. for 10 min. The PCR product (with a size of about 300 bp) was digested with Bgl II and Pst I after recovered by gel cutting. The digestion system comprised: PCR product: 15 µl, 10× bufferH: 4 µl; Bgl II and Pst I enzymes (TaKaRa): 2 µl each; H₂O: 27 µl. The digestion was carried out at 37° C. for 8 h or longer followed by recovering of the digested fragment. The resultant fragment was ligated to vector pEGFP-N1 digested with the same enzymes. The positive clones were screened by digesting and sequencing, designated as pEGFP-HR1. MDCK cells were transfected with vector pEGFP-HR1 by the liposome method. The cells were screened by adding antibiotic G418 (Gibco Inc.) and the stably cloned cells were selected using green fluorescent protein reporter gene, thus providing the MDCK cell line stably expressing HR1-EGFP fusion protein on surface of cells (The schematic diagram of protein expression was shown in FIG. 7. The cells screened for stably expressing clones were shown in FIG. 8A, wherein the green portion showed the expressed HR1-EGFP fusion protein and the arrow only demonstrated one of them).

2) Construction of pEGFP-HR2 Expression Vector

The coding sequence of HR2 is 153 bp, and this fragment of interest may be obtained directly by PCR. The primers were synthesized as follows:

```
P17: CGGGATCCAGGAGAATAGAAAATTTAAAC  (SEQ ID NO: 35)
P18: CGGAATTCCTGTAGTCGGACCTTGTCG    (SEQ ID NO: 36)
```

Figure 8C:
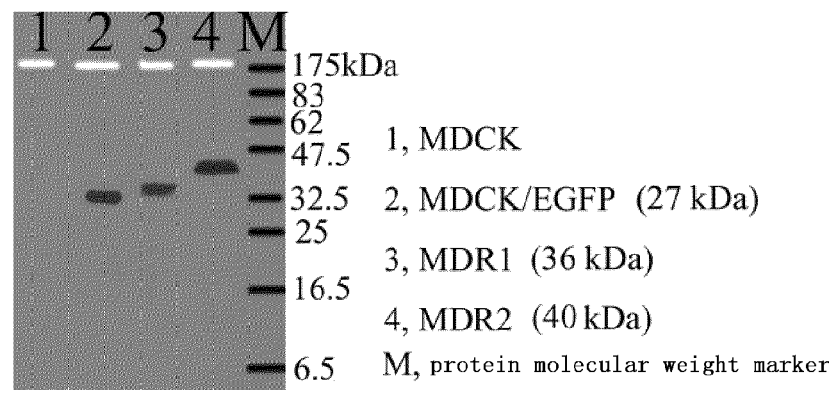
FIG. 8C: Western-Blotting assay of the MDCK cells stably expressing the fusion proteins HR1-EGFP and HR2-EGFP, respectively. Anti-EGFP antibody (1:2000) is used in this assay. MDCK: the negative control of MDCK cells, wherein no band is detected; MDCK/EGFP: the MDCK cell transfected with an empty vector of pEGFP-N1 is used as the positive control, wherein a band of approximately 27 kDa which is same as the size expected for EGFP protein is detected; MDR1: MDCK cells stably expressing the fusion protein HR1-EGFP, wherein a protein band of approximately 36 kDa which is same as the size expected for this fusion protein is detected; MDR2: MDCK cells stably expressing the fusion protein HR2-EGFP, wherein a protein band of approximately 40 kDa which is same as the size expected for this fusion protein is detected.

The fragment of interest of HR2 (153 bp; as shown in SEQ ID NO:13) was obtained by PCR using the above primers and the HA gene (SEQ ID NO:37) cloned in Example 1 as a templet. The used PCR system comprised: H₂O: 16 µl; 10×pfu buffer: 2.5 µl; dNTPs: 2.5 µl; P17 and P18 (10 µM): 1 µl each; templet pGEM-HA: 1 µl; pfu Taq enzyme: 1 µl. PCR reaction procedure included: one cycle of 94° C. for 4 min; 32 cycles of 94° C. for 30 s; 62° C. for 30 s; 72° C. for 30 s; and then final extension at 72° C. for 10 min. After digested with BamH I and EcoR I, the PCR product was ligated to pcDNA-HR1 (recovering vector framework) vector digested with the same enzymes. Positive clones of pcDNA-HR2 were obtained by screening. Fragment SP-HR2-MSD was obtained by PCR using P15 and P16 as primers and pcDNA-HR2 as the templet. The used PCR system comprised: H₂O: 16 µl; 10×pfu buffer: 2.5 µl; dNTPs: 2.5 µl; P15 and P16 (10 µM): 1 µl each; templet pcDNA-HR2: 1 µl; pfu Taq enzyme: 1 µl. PCR reaction procedure included: one cycle of 94° C. for 4 min; 32 cycles of 94° C. for 30 s; 64° C. for 30 s; 72° C. for 30 s; and then final extension at 72° C. for 10 min. The coding sequence of fragment SP-HR2-MSD was shown in SEQ ID NO:38. After digested with Bgl II and Pst I, the PCR product was ligated to pEGFP-HR1 (recovering vector framework) vector digested with the same enzymes. Positive clones were screened out by digesting and sequencing and designated as pEGFP-HR2. MDCK cells were transfected with vector pEGFP-HR2 by the liposome method. The cells were screened by adding antibiotic G418 and the stably cloned cells were selected using green fluorescent protein reporter gene, thus providing the MDCK cell line stably expressing HR2-EGFP fusion protein on surface of cells (The schematic diagram of protein expression was shown in FIG. 7. The cells screened for stably expressing clones were shown in FIG. 8B, wherein the green portion showed the expressed HR2-EGFP fusion protein and the arrow only demonstrated one of them). Western-Blotting assays were performed for MDCK cells, MDCK cells transfected with an empty vector pEGFP-N1, stably cloned MDCK cells (MDR1) expressing HR1-EGFP fusion protein and stably cloned MDCK cells (MDR2) expressing HR2-EGFP fusion protein, so as to confirm the expression of HR1-EGFP and HR2-EGFP fusion protein in the stably cloned cells (see FIG. 8C).

3) Inhibitory Effect of Stably Cloned MDCK Cells on Formation of Influenza Viral Plaques MDCK cells, stably cloned MDCK cells (MDR1) expressing HR1-EGFP fusion protein and MDCK cells (MDR2) expressing HR2-EGFP fusion protein were inoculated into a 6-well plate and cultured in DMEM culture medium for 24-36 hours until 100% confluence. Supernatant was discharged, and cells were washed with PBS twice and serum-free DMEM medium once. QH-WSN and WSN recombinant viruses were diluted to 40 PFU/ml with serum-free DMEM medium respectively. The diluent was added into wells, 1 ml/well, 3 replications for each group, and two of 6-well plates for each experiment. With addition of virus suspension, the cells were incubated at 37☐ for 1 h. Then supernatant was discharged, and cells were washed with PBS twice and serum-free DMEM medium once, so as to remove the virions which were not adsorbed. The following procedures of the plaque experiment were carried out according to those in "Example 3". Once plaques became clear, their number was counted. Each well was counted for at least twice, in order to avoid error. Each group of experiments was performed in triplicate at least. The inhibitory rate of plaques was calculated for the stably cloned cells in accordance with the following formula: Inhibitory rate(%)=(number of plaques in the group of MDCK cells−number of plaques in the group of cells expressing HR1/2−EGFP fusion protein)/number of plaques in the group of MDCK cells×100%.

Figure 9A:
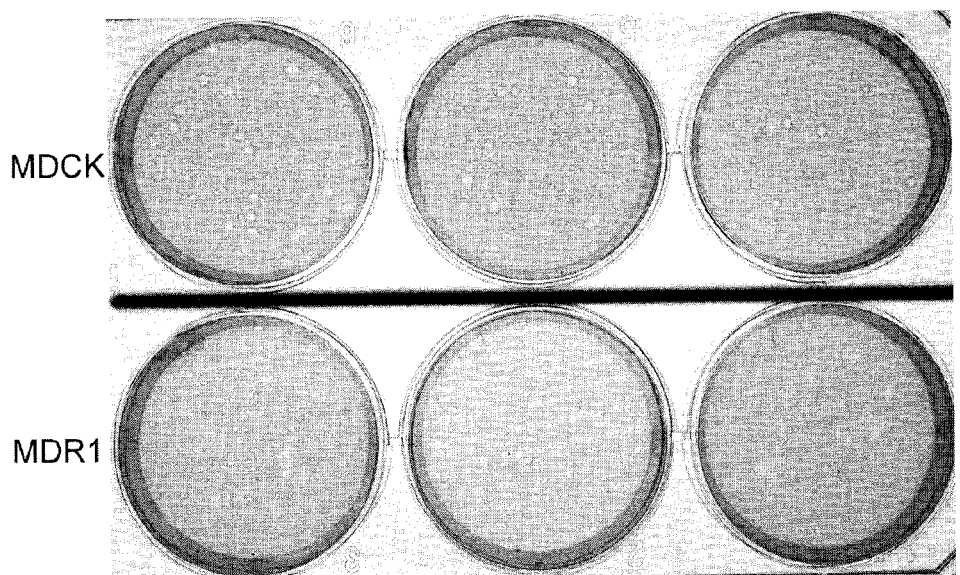
FIG. 9A: The plaque formed by QH-WSN avian influenza virus on MDCK cells and the MDR1 cells stably expressing the fusion protein HR1-EGFP.
Figure 9B:
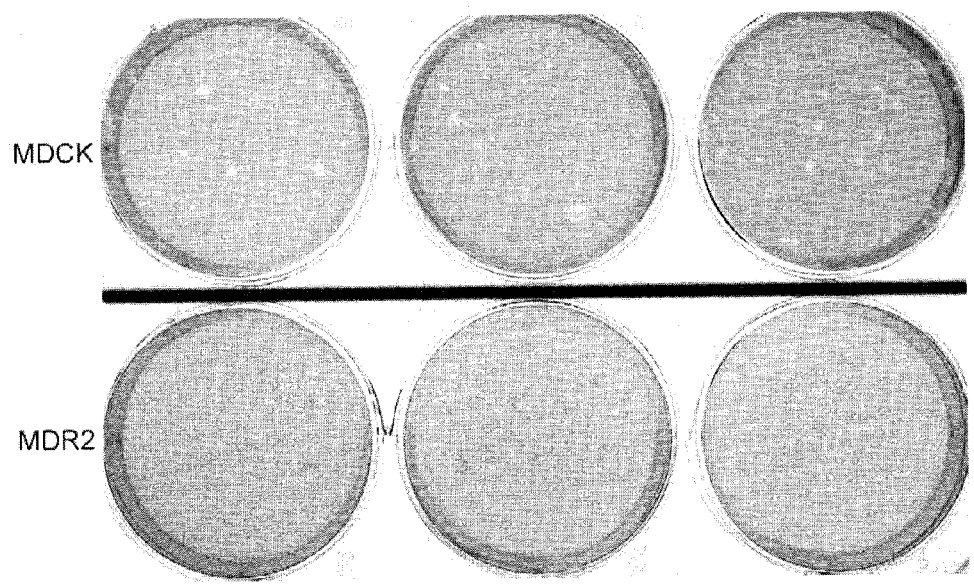
FIG. 9B: The plaque formed by QH-WSN avian influenza virus on MDCK cells and the MDR2 cells stably expressing the fusion protein HR2-EGFP.
Figure 10:
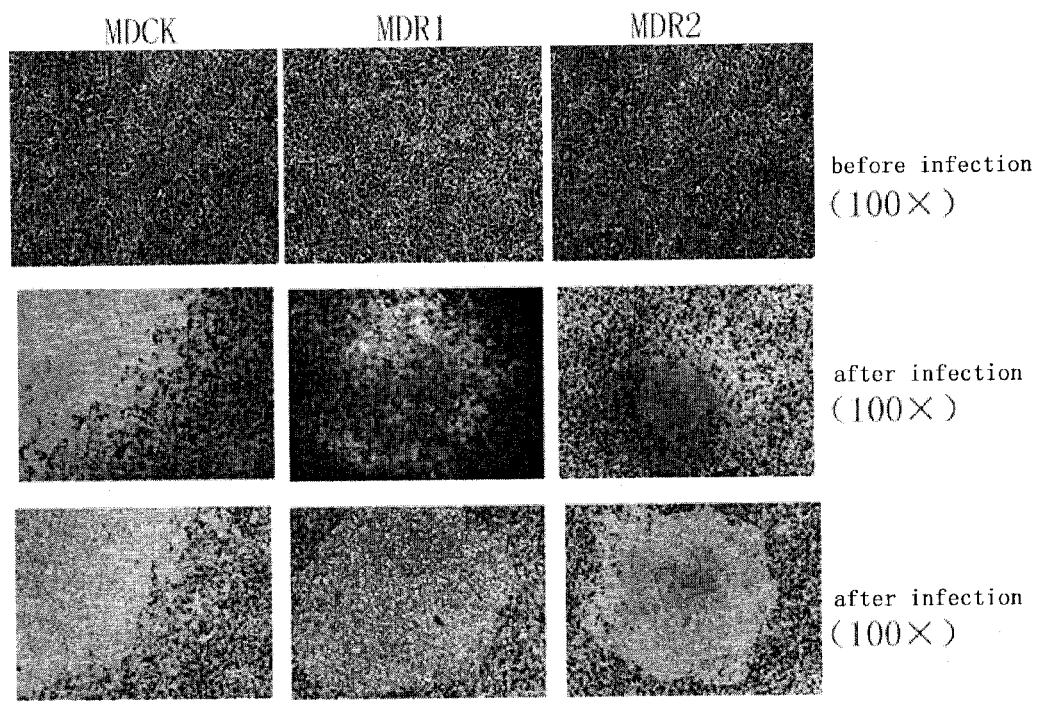
FIG. 10: Size of the plaque formed by WSN human influenza virus on MDCK cells and the MDR1/2 cells stably expressing the fusion protein HR1/2-EGFP. MDCK: normal MDCK cells; MDR1: MDCK cells stably expressing the fusion protein HR1-EGFP; MDR2: MDCK cells stably expressing the fusion protein HR2-EGFP. The first line shows the cell status before infection of WSN human influenza virus (100× indicates this image is photographed after being magnified 100 diameters, same as below); whereas the second and third lines show the plaque formed after infection of human influenza virus WSN (100× magnification). Because the size of the plaque formed on MDCK cell by infection of human influenza virus WSN is relative big, only ¼ of the plaque is photographed after a 100× magnification. From this Figure, it can be seen that the plaque formed on MDCK cell by infection of human influenza virus WSN is bigger than that those formed on MDR1 and MDR2 cells.

The result showed that the stably cloned cells expressing HR1-EGFP or HR2-EGFP fusion protein were able to effectively inhibit the infection of influenza virus (including human influenza WSN virus and avian influenza QH-WSN virus). The number of plaques formed by viruses was reduced on the MDCK cells which expressed HR1 or HR2 fusion protein (see FIGS. 9A and 9B), and the size of the most formed plaques was relatively small (the representative results were shown in FIG. 10). The statistic results indicated that the plaque inhibitory rate of QH-WSN virus by MDR1 was 25±10.0%; the plaque inhibitory rate of QH-WSN virus by MDR2 was 57.8±8.0%; the plaque inhibitory rate of WSN virus by MDR1 was 11.0±5.2%; and the plaque inhibitory rate of QH-WSN virus by MDR2 was 43.0±19.1%. In view of the above, the HR1 and HR2 expressed outside cell membrane had a certain inhibitory effect on both of these two types of influenza viruses, wherein the inhibitory effect of HR2 was stronger. The two types of fusion protein had a stronger inhibitory effect on QH-WSN than on WSN, indicating that the inhibitory effect of HR1 and HR2 had some specificity. And HR1 and HR2 had a certain level of crossing inhibitory effect on homologous sequences, which indicated that such polypeptide medicine could be widely used for inhibiting various subtypes of influenza viruses.

Example 9

Inhibitory Effect of Recombinantly Expressed Protein HR12121 on Formation of Influenza Viral Plaques 1) Construction of Prokaryotic Expression Vector pET-HR12121

The following primers were used in the process of construction of the expression vector:

```
                                        (SEQ ID NO: 39)
P19: GGAATTCCATATGTCAGGTGGAGGTACCAGGAGAATAGAAAAT
(comprising Nde I and Kpn I digestion sites
underlined; the following digestion sites are
underlined too)

(SEQ ID NO: 40)
P20: CGGGATCCCGAACTACCGCCCGAGCTTCCACCTGAACTGCCACCC
TGTAGTCG GACCTT
(comprising BamH I site and linker2)

(SEQ ID NO: 41)
P21: CGGAATTCGGTGGCAGTTCAGGTGGAAGCTCGGGCGGTAGTTCGA
GGAGAATAGAAAAT
(comprising EcoR I site and linker1)

(SEQ ID NO: 42)
P22: CCGCTCGAGACCTCCGCTAGATCTCTGTAGTCGGACCTTGTC
(comprising Xho I and Bgl II sites)

(SEQ ID NO: 43)
P23: GGAATTCCATATGAAAGAATCCACTC
(comprising Nde I site)

(SEQ ID NO: 44)
P24: GGGGTACCTGAGCTGGACGAACTACCGCCC
(comprising Kpn I site)

(SEQ ID NO: 45)
P25: GAAGATCTTCAAGCTCCGGTGGCAGTTCAG
(comprising Bgl II site)

(SEQ ID NO: 46)
P26: CCGCTCGAGTTTGTCAATGATCGAG
(comprising Xho I site)
```

The process for constructing the expression vector was shown as follows:

Step 1. Fragment Nde I-Kpn I-HR2-Linker2-BamH I (225 bp in length) was obtained by PCR using pcDNA-HR2 as the templet, and P19 and P20 as primers. The used PCR system comprised: H$_2$O: 16 μl; 10×pfu buffer: 2.5 μl; dNTPs: 2.5 μl; P19 and P20 (10 μM): 1 μl each; templet pcDNA-HR2: 1 μl; pfu Taq enzyme: 1 μl. PCR reaction procedure included: one cycle of 94° C. for 4 min; 32 cycles of 94° C. for 30 s, 58° C. for 30 s, 72° C. for 30 s; and one cycle of 72° C. for 10 min. The fragment of interest was digested with Nde I and BamH I after recovered by gel cutting and ligated into pET-30a vector (Novagen) framework digested with the same enzymes, in order to provide plasmid pET-HR2-Linker2. The order of the relevant digestion sites on pET-HR2-Linker2 was Nde I-Kpn I-HR2-Linker2-BamH I.

Step 2. Fragment EcoR I-Linker1-HR2-Bg/II Xho I (221 bp in length) was obtained by PCR using pcDNA-HR2 as the templet, and P21 and P22 as primers. The used PCR system comprised: H$_2$O: 16 μl; 10×pfu buffer: 2.5 μl; dNTPs: 2.5 μl; P21 and P22 (10 μM): 1 μl each; templet pcDNA-HR2: 1 μl; pfu Taq enzyme: 1 μl. PCR reaction procedure included: one cycle of 94° C. for 4 min; 32 cycles of 94° C. for 30 s, 56° C. for 30 s, 72° C. for 30 s; and one cycle of 72° C. for 10 min. The fragment of interest was digested with EcoR I and Xho I after recovered by gel cutting and ligated into pcDNA-HR1 vector framework digested with the same enzymes, in order to provide plasmid pcDNA-HR1-Linker1-HR2. The order of the relevant digestion sites on pcDNA-HR1-Linker1-HR2 was BamH I-HR1-EcoR I-Linker1-HR2-Bgl II Xho I.

Step 3. Fragment HR1-Linker1-HR2 (281 bp in length) was recovered by digestion of pcDNA-HR1-Linker1-HR2 with BamH I and Xho I, and ligated into pET-HR2-Linker2 plasmid framework digested with the same enzymes. Plasmid pET-HR2-Linker2-HR1-Linker1-HR2 was obtained by screening, and designated as pET-HR212. The order of the relevant digestion sites on pET-HR212 was Nde I-Kpn I-HR2-Linker2-BamH I-HR1-EcoR I-Linker1-HR2-Bgl II-Xho I.

Step 4. Fragment Nde I-HR1-Linker1-Kpn I (135 bp in length) was obtained by PCR using plasmid pET-HR212 as the templet, and P23 and P24 as primers. The used PCR system comprised: H$_2$O: 16 μl; 10×pfu buffer: 2.5 μl; dNTPs: 2.5 μl; P23 and P24 (10 μM): 1 μl each; templet pET-HR212: 1 pfu Taq enzyme: 1 μl. PCR reaction procedure included: one cycle of 94° C. for 4 min; 32 cycles of 94° C. for 30 s, 56° C. for 30 s, 72° C. for 30 s; and one cycle of 72° C. for 10 min. The fragment of interest was digested with Nde I and Kpn I after recovered by gel cutting and ligated into pET-HR212 vector framework digested with the same enzymes, in order to provide plasmid pET-HR1-Linker1-HR2-Linker2-HR1-Linker1-HR2, which was designate as pET-HR1212. The order of the relevant digestion sites on pET-HR1212 was Nde I-HR1-Linker1-Kpn I-HR2-Linker2-BamH I-HR1-EcoR I-Linker1-HR2-Bgl II-Xho I.

Step 5. Fragment Bgl II-Linker2-HR1-Xho I (131 bp in length) was obtained by PCR using plasmid pET-HR212 as the templet, and P25 and P26 as primers. The used PCR system comprised: H₂O: 16 µl; 10×pfu buffer: 2.5 µl; dNTPs: 2.5 µl; P25 and P26 (10 µM): 1 µl each; templet pET-HR212: 1 pfu Taq enzyme: 1 µl. PCR reaction procedure included: one cycle of 94° C. for 4 min; 32 cycles of 94° C. for 30 s, 56° C. for 30 s, 72° C. for 30 s; and one cycle of 72° C. for 10 min. The fragment of interest was digested with Bgl II and Xho I after recovered by gel cutting and ligated into pET-HR1212 vector framework digested with the same enzymes, in order to provide plasmid pET-HR1-Linker1-HR2-Linker2-HR1-Linker1-HR2-Linker2-HR1. This plasmid was confirmed to comprise a completely correct sequence (SEQ ID NO:47) by sequencing, and designate as pET-HR12121. The order of the relevant digestion sites on pET-HR12121 was Nde I-HR1-Linker1-Kpn I-HR2-Linker2-BamH I-HR1-EcoR I-Linker1-HR2-Bgl II-Linker2-HR1-Xho I.

2) Recombinant Expression and Purification of Polyhelix Protein HR12121 in *E. coli* BL21

Figure 11A:
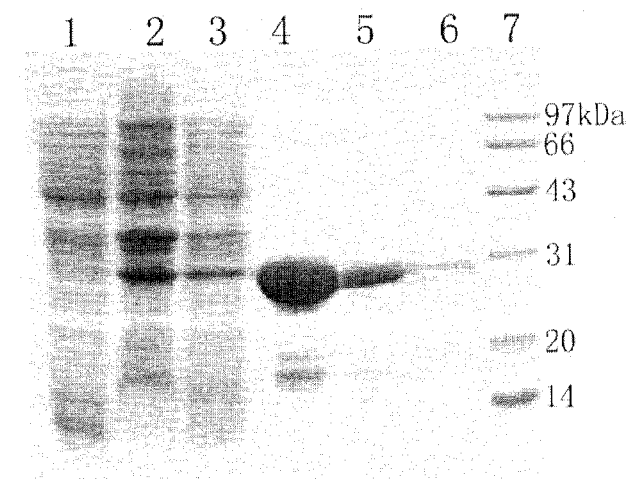
FIG. 11A: The SDS-PAGE assay of expression and purification of recombinant protein HR12121. 1: the expression product induced by an empty vector BL21/pET-30a; 2: the bacterial precipitation after 12-hour expression induced by BL21/pET-HR12121 at 16° C.; 3: the supernatant of the bacterial lysate after 12-hour expression induced by BL21/pET-HR12121 at 16° C.; 4-6: the protein of interest with a size of approximately 25 kDa eluted for 3 times (The eluant is 200 mM Tris; 20 mM NaCl; 200 mM imidazole); 7: the protein molecular weight marker, with the numbers on the right showing protein molecular weights in a unit of kDa.
Figure 11B:
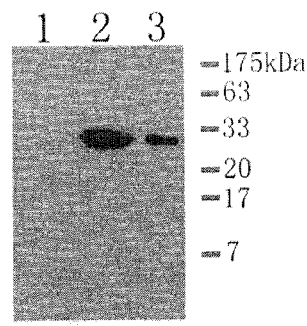
FIG. 11B: The Western-Blotting assay of expression and purification of recombinant protein HR12121. Anti-His antibody (1:5000) is used in this assay. 1: the bacterial lysate before induction by BL21/pET-HR12121; 2: the supernatant of the bacterial lysate after 12-hour expression induced by BL21/pET-HR12121 at 16° C.; 3: protein HR12121 purified from the supernatant (100× dilution). The numbers on the right show protein molecular weights in a unit of kDa.

Prokaryotic expression vector pET-HR12121 was transformed into *E. coli* expression host BL21 (DE3). A single colony was picked and inoculated into 50 ml LB culture medium. After addition of kanamycin to a final concentration of 50 µg/ml, culture was carried out at 37° C. for 8 h. Subsequently the culture was transferred into 4 L fresh LB culture medium in a ratio of 1:100. Kanamycin was added to a final concentration of 50 µg/ml, and then culture was carried out at 37° C. for 2-2.5 h. Once the value of $OD_{600}$ reaching 0.35-0.4, the bacterial solution was cooled to 16° C. After addition of inducer IPTG to a final concentration of 0.8 mM, the bacterial solution was cultured at 16° C. for 12 h, in order to induce the expression of protein of interest. On the other hand, a small amount of pET-30a transformed into BL 21 was induced as a negative control. After lysis of the bacteria, SDS-PAGE assay was conducted and showed that after induction, a large amount of interested protein HR12121 was expressed, accounting for approximately 15% of total protein amount of bacteria. Following suspension and ultrasonic lysis (the ultrasonic condition was 50 continuous ultrasonic treatments of 4 s, with an interval of 12 s, which was repeated 4 times after cooling for 10 min) of bacteria in a lysis buffer (200 mM Tris; 20 mM NaCl), the lysate was centrifuged at 4° C. for 15 min (15000 r/m). Expression of the interested protein was detected in both the supernatant and the precipitate (see FIG. 11A). The centrifuged supernatant was combined with Ni⁺ beads at 4° C. for 2 h or longer, and rinsed with the lysis buffer until no protein impurity outflow. The protein of interest was eluted with the lysis buffer containing 200 mM imidazole. The elution was collected in 3 separate containers, 15 ml each. SDS-PAGE was performed to test purification effect of the protein (see FIG. 11A). Purity of the interested protein was 95% or more after purification. After the protein was concentrated through an ultrafiltration tube and bacteria were removed through a 0.22 µM sterile filtration membrane, the protein concentration was 6.2 mg/ml or 250 µM. It was shown in the Western-Blotting assay that anti-His antibodies could specifically bind to protein with a size of approximately 25 kDa, and the size of the detected protein corresponded to that of the protein of interest (24.8 kDa) (see FIG. 11B).

Figure 12:
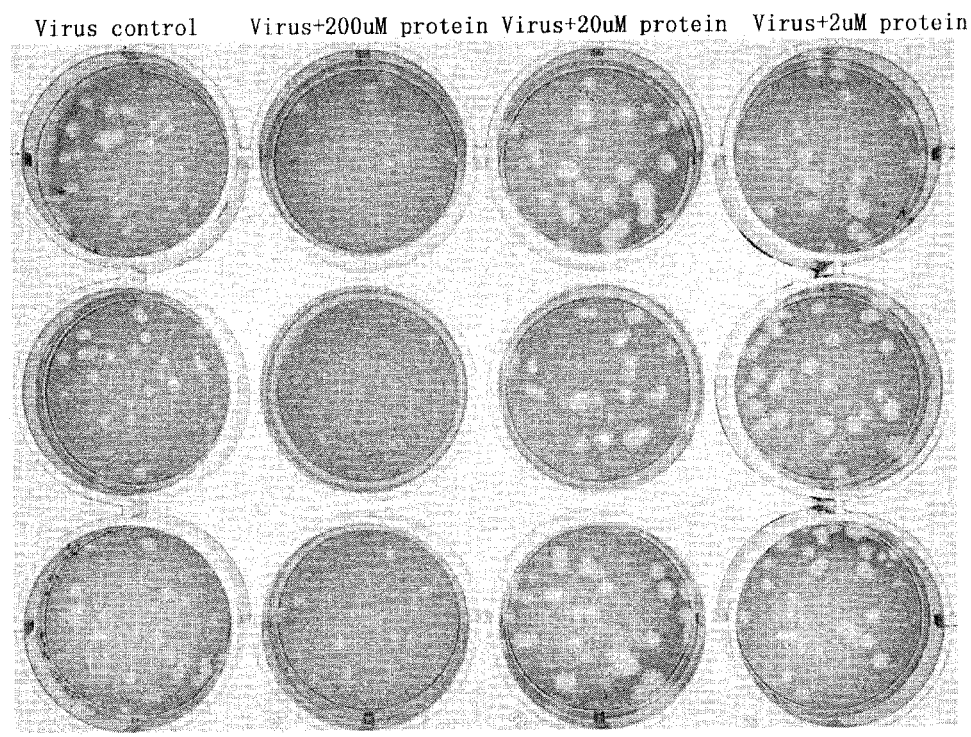
FIG. 12: Inhibitory effect of the recombinantly expressed and purified protein HR12121 on the plaque of JX human influenza virus. Virus control: the plaque control generated after infection of cells with only virus but not polypeptide; virus+peptide: the cells infected with a combination of virus and protein at different concentration (The final concentration of the protein is 200, 20 and 2 μM respectively).

3) Inhibitory Effect of Polyhelix Protein HR12121 on Formation of Influenza Viral Plaques In accordance with the procedures in section 2) of Example 4, inhibitory effect of recombinant expression protein HR12121 on plaques formed on MDCK by influenza virus strains QH-WSN, WSN and JX was detected. The recombinant protein was serially diluted to a final concentration of 400, 40, or 4 µM respectively, and combined with an equal amount of virus. Plaque test was performed, which showed a representative result in FIG. 12. The statistic results showed that $IC_{50}$ of HR12121 was 53.8±14.1 µM for plaque formation of avian influenza virus QH-WSN; 53.3±22.6 µM for plaque formation of human influenza virus WSN; and 28.0±16.3 µM for plaque formation of human influenza virus JX.

Conclusion:

The above Examples showed that chemically synthesized HR1 or HR2 polypeptide, mutated HR1-1 and HR1-2 polypeptides, fragmentally synthesized HR2A, HR2B and HR2C polypeptides, HR1 polypeptide combined with other polypeptides (such as HR2A polypeptide, HR2B polypeptide or HR2C polypeptide), recombinantly expressed HR12121 protein, HR1-EGFP fusion protein and HR2-EGFP fusion protein expressed on eukaryotic cell membrane all inhibited infection of host cells with the highly pathogenic avian influenza virus (H5N1 subtype) and human influenza virus (H1N1 subtype and H3N2 subtype). Therefore, the polypeptide and protein of the invention could be used as a specified anti-influenza virus infection inhibitor.

REFERENCE

Abed Y, Baz M, Boivin G. Impact of neuraminidase mutations conferring influenza resistance to neuraminidase inhibitors in the N1 and N2 genetic backgrounds. Antivir Ther. 2006, 11(8):971-6.

Das A T, Brummelkamp T R, Westerhout E M, Vink M, Madiredjo M, Bernards R, Berkhout B. Human immunodeficiency virus type 1 escapes from RNA interference-mediated inhibition. J Virol. 2004, 78(5):2601-5.

de Jong M D, Tran T T, Truong H K, Vo M H, Smith G J, Nguyen V C, Bach V C, Phan T Q, Do Q H, Guan Y, Peiris J S, Tran T H, Farrar J. Oseltamivir resistance during treatment of influenza A (H5N1) infection. N Engl H Med. 2005, 353(25):2667-72.

Gao Y, Sun L, Dong J, Xu X, Shu Y, Chen M, Yin L, Liang Z, Jin Q. Rapid identification of small interfering RNA that can effectively inhibit the replication of multiple influenza B virus strains. Antivir Ther. 2006, 11(4):431-8.

Gaush C R, Hard W L, Smith T F. Characterization of an established line of canine kidney cells (MDCK). Proc Soc Exptl Biol Med. 1966, 122(3):931-5.

Greenberg M, Cammack N, Salgo M, Smiley L. HIV fusion and its inhibition in antiretroviral therapy. Rev Med. Virol. 2004, 14(5):321-37.

Jefferson T, Demicheli V, Rivetti D, Jones M, Di Pietrantonj C, Rivetti A. Antivirals for influenza in healthy adults: systematic review. Lacent. 2006, 367(9507):303-13.

Kamps B S, Hoffmann C, Preiser W Influenza report 2006. 2006, Fly Publisher, Paris, France.

Leneva I A, Goloubeva O, Fenton R J, Tisdale M, Webster R G. Efficacy of zanamivir against avian influenza A viruses that possess genes encoding H5N1 internal proteins and are pathogenic in mammals. Antimicrob Agents Chemother. 2001, 45(4):1216-24.

Liu J, Xiao H, Lei F, Zhu Q, Qin K, Zhang X W, Zhang X L, Zhao D, Wang G, Feng Y, Ma J, Liu W, Wang J, Gao G F. Highly pathogenic H5N1 influenza virus infection in migratory birds. Science. 2005, 309(5738):1206.

Neumann G, Watanabe T, Ito H, Watanabe S, Goto H, Gao P, Hughes M, Perez D R, Donis R, Hoffmann E, Hobom G, Kawaoka Y. Generation of influenza A viruses entirely from cloned cDNAs. Proc Natl Acad Sci USA. 1999, 96 (16):9345-50.

Skehel J J. Influenza virus. Amantadine blocks the channel. Nature. 1992, 358(6382):110-1.

Wang E, Sun X, Qian Y, Zhao L, Tien P, Gao G F. Both heptad repeats of human respiratory syncytial virus fusion protein are potent inhibitors of viral fusion. Biochem Biophys Res Commun. 2003, 302(3):469-75.

Young J K, Li D, Abramowitz M C, Morrison T G Interaction of peptides with sequences from the Newcastle disease virus fusion protein heptad repeat regions. J Virol. 1999, 73(7):5945-56.

Guo Y J, Cheng X W, Influenza viruses and experimental techniques thereof 1997, China Sanxia press, Beijing, China.

Lan Y, Li X, Dong L B, Zhang Y, Wen L Y, Zhang Y M, Wang M, Guo Y J, and Shu Y L, Adamantane resistance among influenza (H3N2) viruses isolated from the mainland of China. Chinese Journal of Experimental and Clinical Virology. 2006, 20(2):21-23.

Pang H L, Li Z L, Gong L B, The advance in a study on the anti-influenza virus effect of traditional Chinese and western medicine. Chinese Journal of Clinical Medicine. 2004, 5(1):84-6.

Zhang W M, Yang Z Q, Qin S Z, The advance in a study on anti-virus effect of traditional Chinese herbs. Progress in Veterinary Medicine. 2001, 22(4):16-21.

What is claimed is:

1. An isolated polypeptide, wherein the amino acid sequence of said polypeptide consists of SEQ ID NO: 1, 2, 3, 4, 5, 21, 22 or 23.

2. An isolated polypeptide comprising:
   (a) a first polypeptide consisting of SEQ ID NO: 1, 2 or 3;
   (b) a second polypeptide consisting of SEQ ID NO: 4, 5, 21, 22 or 23; and
   (c) an exogenous linking peptide that connects said first and second polypeptides, said linking peptide comprising at least one of glycine, serine, proline, and alanine.

3. A polypeptide according to claim 2, wherein the amino acid sequence of said linking peptide is selected from the group consisting of SEQ ID NO: 6-10.

4. A polypeptide according to claim 2, wherein the amino acid sequence of said polypeptide consists of the amino acid sequence of SEQ ID NO: 11.

5. A polypeptide of claim 2, further linked with a tag used for protein detection and purification.

6. A polypeptide of claim 5, wherein said tag is selected from the group consisting of EGFP, His6, GST, MBP and Nus.

7. A pharmaceutical composition comprising a therapeutically effective amount of a polypeptide of claim 1 and a pharmaceutically acceptable carrier.

8. A process for treating infection by influenza virus, comprising administering to a subject in need thereof a therapeutically effective amount of a polypeptide of claim 1.

9. A kit for treating influenza, comprising a polypeptide of claim 1, and an instruction.

10. A pharmaceutical composition comprising a therapeutically effective amount of a polypeptide of claim 2 and a pharmaceutically acceptable carrier.

11. A process for treating infection by influenza virus, comprising administering to a subject in need thereof a therapeutically effective amount of a polypeptide of claim 2.

12. A kit for treating influenza, comprising a polypeptide of claim 2, and an instruction.

\* \* \* \* \*